(12) United States Patent
Caminade et al.

(10) Patent No.: US 6,939,831 B1
(45) Date of Patent: Sep. 6, 2005

(54) PESTCIDE AND/OR PLANT GROWTH REGULATING COMPOSITIONS

(75) Inventors: Anne-Marie Caminade, Toulouse (FR); Fabienne Gauffre-Guirardel, Pessac (FR); Jean-Pierre Majoral, Ramonville Saint-Agne (FR); Christelle Marmillon, Montpellier (FR)

(73) Assignee: Aventis Cropscience S.A. (FR)

( * ) Notice: Subject to any disclaimer, the term of this patent is extended or adjusted under 35 U.S.C. 154(b) by 0 days.

(21) Appl. No.: 09/936,119

(22) PCT Filed: Mar. 7, 2000

(86) PCT No.: PCT/FR00/00557

§ 371 (c)(1),
(2), (4) Date: Feb. 1, 2002

(87) PCT Pub. No.: WO00/53009

PCT Pub. Date: Sep. 14, 2000

(30) Foreign Application Priority Data

Mar. 8, 1999 (FR) ............................................. 99 02975

(51) Int. Cl.[7] ........................ A01N 25/12; A01N 25/00
(52) U.S. Cl. ...................... 504/367; 514/789; 514/944; 424/DIG. 16
(58) Field of Search ................................. 504/116, 367, 504/116.1; 424/DIG. 16; 514/789, 944

(56) References Cited

U.S. PATENT DOCUMENTS 5,560,929 A * 10/1996 Hedstrand et al. .......... 424/486

FOREIGN PATENT DOCUMENTS

| CN | 1138945 | * | 1/1997 |
| FR | 2734268 | | 11/1996 |
| WO | 88/01179 | | 2/1988 |

OTHER PUBLICATIONS

D. Prévoté, et al., "Application Of The Horner–Wadsworth––Emmons Reaction To The Functionalization Of Dendrimers: Synthesis Of Amino Acid Terminated Dendrimers", *Synthesis.*, No. 10, 1997, pp. 1199–1207.

* cited by examiner

*Primary Examiner*—Alton Pryor
(74) *Attorney, Agent, or Firm*—Ostrolenk, Faber, Gerb & Soffen, LLP

(57) ABSTRACT

The invention concerns pesticide and/or insecticide and/or plant growth regulating compositions comprising specific dendrimers, said compositions being, in particular, useable for agriculture and/or public health or domestic hygiene; the invention also concerns methods for treating and/or protecting crops and/or for public health and domestic hygiene using said compositions. The invention further concerns specific dendrimers.

29 Claims, No Drawings

PESTCIDE AND/OR PLANT GROWTH REGULATING COMPOSITIONS

DESCRIPTION

The present invention relates to pesticide and/or insecticide and/or plant growth regulating compositions comprising specific dendrimers, said compositions being, in particular, usable in the fields of agriculture, and/or public health or domestic hygiene, and to methods for treating and/or protecting crops and/or for public health or domestic hygiene using said compositions, and methods for preparing such compositions, or specific dendrimers.

Many pesticide and/or insecticide and/or plant growth regulating compositions are known, in particular from French or European patents or patent applications EP-869 712, FR-2 733 502, EP-854 676, EP-851 729, EP-823 212, and the like.

The documents, French, European or international patents or applications WO-88/01179, FR-2 734 268, FR-2 761 601, EP-765 357, EP-736 059, EP 726 502 or the publication *Synthesis*, no. 10, 1997, pages 1199–1207, describe uses of dendrimers.

An object of the present invention is to provide compositions comprising a dendrimer capable of forming a gel combined with a pesticide and/or insecticide and/or plant growth regulating active substance and which can be used for agriculture and/or for public health or domestic hygiene, said compositions being in the form of a gel.

An object of the present invention is to provide compositions based on dendrimers capable of forming a gel and whose structure has two types of volume for insertion, in particular of an active substance.

An object of the present invention is to provide compositions based on dendrimers capable of forming a gel and whose structure comprises inner cavities characteristic of the molecules of dendrimers themselves and spaces characteristic of the structure of the gel formed by said dendrimers.

An object of the present invention is to provide compositions in which the active substance is partly located in the inner cavities of the dendrimers used and the remainder in the structure of the gel which said dendrimers form.

An additional object of the present invention is to provide compositions in which at least half of the active substance is located in the structure of the gel formed by the dendrimers used.

An object of the present invention relates to dendrimers with enhanced capacity, in particular dendrimers capable of forming a gel.

Another object of the present invention is to provide pulverulent compositions based on a dendrimer capable of forming a gel and combined with one or more pesticide and/or insecticide and/or plant growth regulating active substances.

An object of the present invention is to provide gelled insecticide compositions based on a dendrimer capable of forming a gel.

An object of the present invention is to provide gelled fungicide compositions based on a dendrimer capable of forming a gel.

An object of the present invention is to provide gelled herbicide compositions based on a dendrimer capable of forming a gel.

An object of the present invention is to provide gelled insecticide and/or plant growth regulating compositions based on a dendrimer capable of forming a gel.

An additional object of the present invention is to provide a method for protecting and/or treating crops using the compositions according to the invention.

Another object of the present invention is to provide compositions in pulverulent form which can be used in the fields of agriculture and/or public health or domestic hygiene, it being possible for said pulverulent compositions to be stored for long periods and in the absence of any precaution, without any substantial impairment of their characteristics.

An object of the present invention is also to provide methods of protection and/or treatment useful for public health or domestic hygiene and using the compositions of the invention, in particular the insecticide compositions and/or compositions for regulating the development of insect and/or animal pests.

An additional object of the present invention is to provide insecticide and/or nematocide and/or acaricide and/or rodenticide baits.

Said insecticide and/or nematocide and/or acaricide and/or rodenticide baits provided in the form of gelled compositions are also a subject of the present invention.

An additional object of the present invention is to provide compositions usable in the fields of agriculture and/or public health or domestic hygiene and exhibiting enhanced stability over time, particularly during long periods of storage and thus to allow the active substance used to retain all its efficacy.

Another object of the present invention is to provide compositions whose handling hazard is very substantially reduced by virtue of their gelled form.

An object of the present invention also relates to compositions in gelled form which are usable in the fields of agriculture and/or public health or domestic hygiene and whose active substance is gradually released.

An additional object of the present invention relates to compositions in gelled form which are usable in the fields of agriculture and/or public health or domestic hygiene and whose active substance is released in a controlled manner.

Another object of the present invention is to provide compositions comprising, in addition to the abovementioned advantages, an increased safety for users and/or for the environment, particularly compositions according to the invention using one or more toxic active substances.

Another object of the present invention is to provide methods for preparing compositions in gelled form which are usable in the fields of agriculture and/or public health or domestic hygiene.

Another object of the present invention is to provide specific dendrimers capable of forming a gel.

COMPOSITIONS ACCORDING TO THE INVENTION

It has now been found that these objectives could be fully or partially achieved by means of the compositions according to the invention which are usable in particular in the fields of agriculture and/or public health or domestic hygiene. Said compositions according to the invention comprise

- one or more active substances which are usable in particular in the fields of agriculture and/or public health or domestic hygiene;
- one or more gellable dendrimers;
- an inorganic or organic liquid carrier.

For the present text, the expression active substance is understood to mean any active substance which can be used for agriculture and/or public health or domestic hygiene, in particular any pesticide active substance and/or any active substance for regulating the development of plants and/or insects or animal pests.

The invention also relates, and this will be presented in greater detail later, to compositions according to the invention which comprise mixtures, associations, combinations or any other form of formulation of several of said active substances.

An essential aspect of the present invention consists in the use of specific dendrimers.

The term dendrimer denotes polymers whose spatial structure adopts an arborescent shape, and the use of a prefix borrowed from Greek and derived from the term dendro meaning tree, to denote this family of polymeric macromolecules having an arborescent structure.

The dendrimers useful for the compositions according to the invention are more particularly macromolecules whose arborescent structure extends in all directions from a central part.

Thus, the dendrimers used in the compositions according to the invention are macromolecules consisting of a central part, termed core of the dendrimer, and to which a series of branched chains, called dendrons, are linked.

FIG. (I) gives a schematic representation of the arborescent structure resembling that of the dendrimers of the compositions according to the invention. Said structure comprises

- a core, most often consisting of a polyfunctional chemical group capable of being linked to a plurality of branched chains or dendrons;
- branches, generally composed of linear or branched organic fragments, linked to each other and to the core, and arborescently organized;
- terminal chemical functional groups, that is to say constituting the peripheral end of said branches;
- inner cavities inherently resulting from the branchings of said branches.

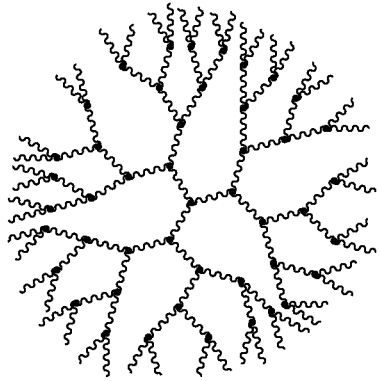

(I)

The schematic representation of FIG. (II) presents FIG. (I) supplemented with a legend, thus allowing a more precise illustration of the components which the arborescent structure, resembling that of the dendrimers of the invention, may comprise.

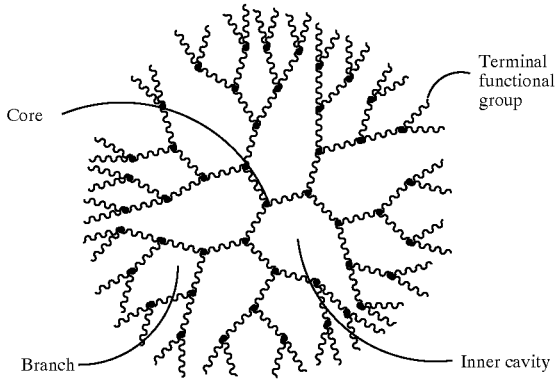

(II)

The organic core is therefore the central part of the dendrimers useful for the compositions according to the invention. It consists, in general, of a chemical group, most often an organic, polyfunctional chemical group capable of being attached to multiple branched chains. The core of the dendrimers of the present invention is also characterized by a multiple valency which corresponds to the number of dendrons to which it is capable of being attached. Details relating to the core of said dendrimers used in the compositions according to the invention will be given in the present text during the detailed description of said dendrimers.

The dendrons of said dendrimers are branched organic chains linked to the core. Generally, said dendrons are series of said branched chains.

The terminal functional groups of the dendrimers useful for the compositions according to the invention are chemical functional groups present at the ends of the dendrons; among the very many chemical functional groups which may constitute said terminal functional groups, there may be mentioned, for example, the ammonium, amidinium, pyridinium, guanidinium or carboxylate functional groups or carboxylic acids. Said terminal functional groups usually confer on said dendrimers some of their characteristics, in particular the possibility of very many individual reactions at the periphery.

The inner cavities of the dendrimers used in the compositions according to the invention inherently result from the existence of the branches of said dendrimers. Said inner cavities allow in particular the inclusion of a variety of substances within the arborescent structure of said dendrimers. However, the size and the accessibility of these inner cavities limits the inclusion of said substances to only molecules whose size and properties are compatible therewith.

For the preparation of the dendrimers useful for the compositions of the present invention, there may be mentioned, mainly, two types of method of synthesis, divergent syntheses and convergent syntheses:

- in the divergent methods, the synthesis is carried out from the core to the periphery by grafting an increasingly large number of small molecules onto the surface of the dendrimer possessing multiple chemical functional groups, a representation of such a route of synthesis is given by scheme (III):
- in the convergent methods, the synthesis is carried out from the periphery toward the core by combining with each other increasingly larger molecules constantly having an available chemical functional group at the level of the core, a representation of such a route of synthesis is given by scheme (IV).

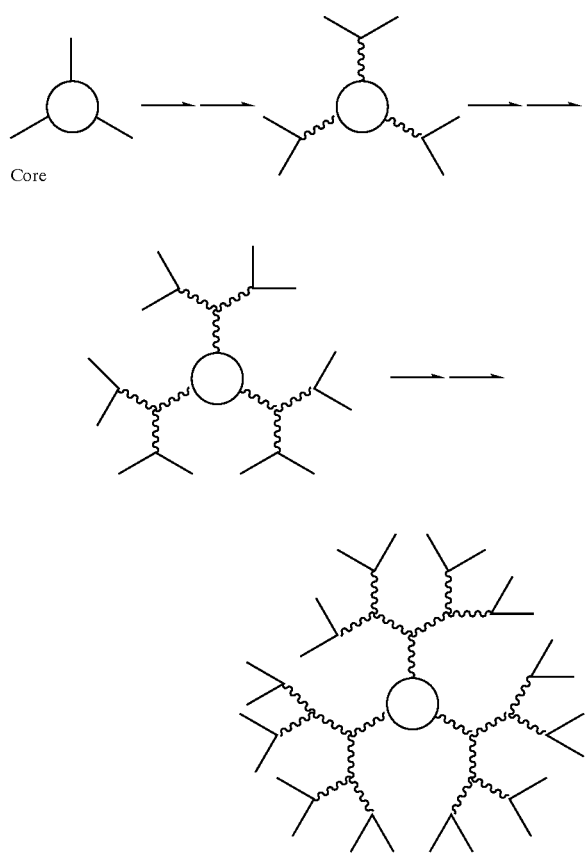

(III)

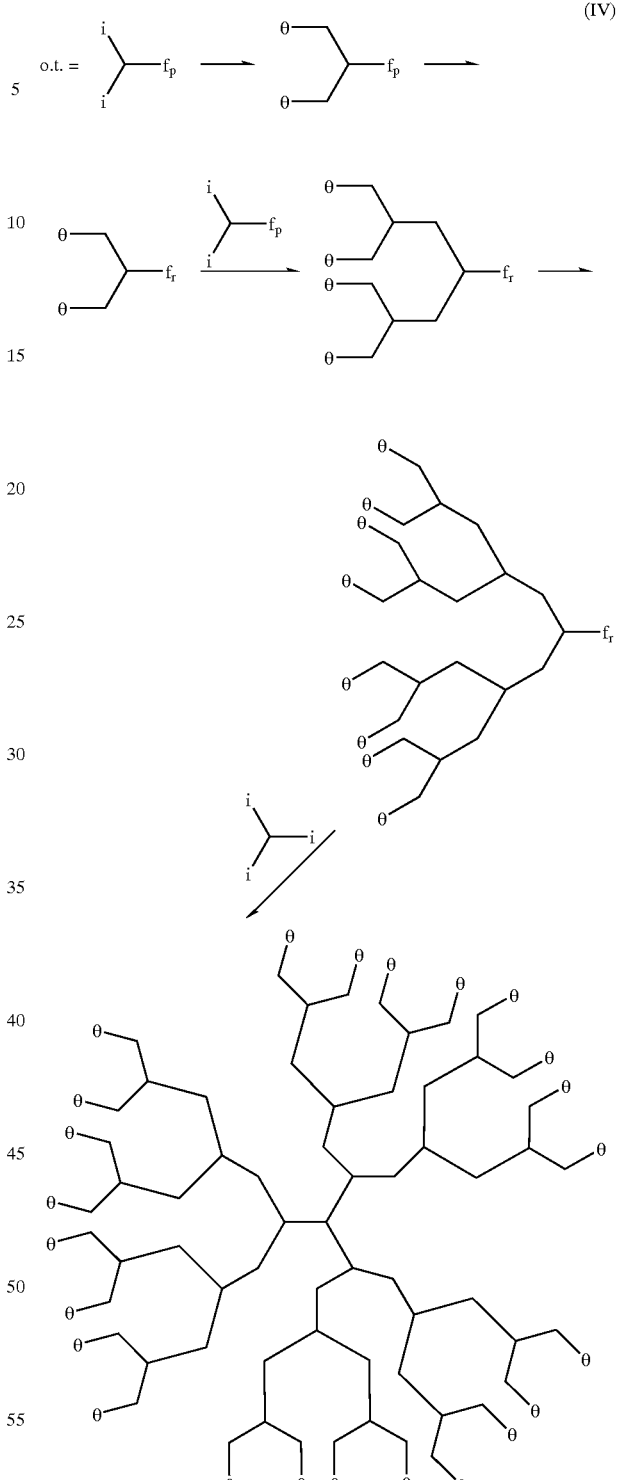

(IV)

$f_r$ = reactive functional group
$f_p$ = protected functional group
$\theta$ = surface
i = inside In addition, using these modes of construction, all the joining points for the branches situated at a similar distance from the core of the dendrimers used for the compositions according to the invention can be defined as forming part of the same generation, each generation may then define, for said dendrimers, layers consisting of these joining points.

Moreover, this mode of constructing the dendrimers, by repetition of steps, is advantageous in that it can allow precise control, inter alia, of their molecular mass, of their size, of their shape and of their capacity to react chemically.

Reference may be made to the various texts of the manual *Les dendrimères* by the ECRIN association, published in June 1998 by the publishers SACER, in which dendrimers are described.

The compositions according to the invention are characterized in that they comprise an active substance as defined above, a dendrimer capable of forming a gel and an inorganic or organic liquid carrier.

In addition and according to the needs or the nature of the disease to be treated, the weed plants, the insect and/or animal pests to be controlled, destroyed or eradicated, or according to the levels of infestation by these pests, or according to the climatic and/or edaphic conditions, the compositions according to the invention may contain any other customary substances for the formulation of compositions useful in the fields of agriculture and/or public health or domestic hygiene.

Among these compounds, there may be mentioned, by way of example, adjuvants, anticaking agents; colorants, thickeners, surfactants, antifoaming compounds, detergents such as alkaline-earth metal salts, dispersants, alkalinizing agents such as bases, bonding agents, emulsifiers, oxidizing agents such as free radical scavengers or catalytic destroyers of hydroperoxides, anticorrosive agents, attractants and/or food substances for the preparation of insecticide baits in particular.

More generally, the compositions according to the invention may comprise any solid or liquid additives corresponding to the usual formulation techniques which are acceptable for uses for agriculture and/or public health or domestic hygiene for example.

These additives may be present in the compositions according to the invention in quantities of between 0 and 50% by weight of said compositions.

Also according to the needs, the nature of the diseases to be treated, of the insect and/or animal pests and/or of the weed plants to be controlled, destroyed or eradicated, the levels of infestation of these pests, the climatic and/or edaphic conditions, the compositions according to the invention may contain one or more combined active substances of the type including fungicides and/or insecticides and/or acaricides and/or rodenticides and/or nematocides and/or insect and/or animal pest repellents and/or agents regulating the development of plants and/or insects and/or one or more herbicide active substances.

In general, the pesticide and/or growth regulating active substances which may enter into the formulation of the compositions according to the invention are those listed in any plant-protection manual, for example L'Index Phytosanitaire (published by the Technical Directorate of the Association de Coordination Technique Agricole or A.C.T.A.) or The Pesticide Manual (by the British Crop Protection Council, edited by Clive Tomlin) or The Electronic Pesticide Manual version 1.1 (by the British Crop Protection Council, edited by Clive Tomlin).

Preferably, and among the fungicide active substances which may be used alone or in combination with other active substances, in particular pesticides, in the compositions according to the invention, there may be mentioned 2-phenylphenol; 8-hydroxyquinoline sulfate; AC 382042; *Ampelomyces quisqualis*; Azaconazole; Azoxystrobin; *Bacillus subtilis*; Benalaxyl; Benomyl; Biphenyl; Bitertanol; Blasticidin-S; Bordeaux mixture; Borax; Bromuconazole; Bupirimate; Calboxin; calcium polysulfide; Captafol; Captan; Carbendazim; Carpropanmid (KTU 3616); CGA 279202; Chinomethionat; Chlorothalonil; Chlozolinate; copper hydroxide; copper naphthenate; copper oxychloride; copper sulfate; cuprous oxide; Cymoxanil; Cyproconazole; Cyprodinil; Dazomet; Debacarb; Dichlofluanid; Dichlomezine; Dichlorophen; Diclocymet; Dicloran; Diethofencarb; Difenoconazole; Difenzoquat; Difenzoquat metilsulfate; Diflumetorim; Dimethirimol; Dimethomorph; Diniconazole; Diniconazole-M; Dinobuton; Dinocap; diphnenylamine; Dithianon; Dodemorph; Dodemorph acetate; Dodine; Dodine free base; Edifenphos; Epoxiconazole (BAS 480F); Ethasulfocarb; Ethirimol; Etridiazole; Famoxadone; Fenamidone; Fenarimol; Fenbuconazole; Fenfin; Fenfuram; Fenhexamid; Fenpiclonil; Fenpropidin; Fenpropimorph; Fentin acetate; Fentin hydroxide; Ferbam; Ferimzone; Fluazinam; Fludioxonil; Fluoroimide; Fluquinconazole; Flusilazole; Flusulfamide; Flutolanil; Flutriafol; Folpet; formaldehyde; Fosetyl; Fosetyl-aluminum; Fuberidazole; Furalaxyl; *Fusarium oxysporum; Gliocladium virens*; Guazatine; Guazatine acetates; GY-81; hexachlorobenzene; Hexaconazole; Hymexazol; ICIA0858; IKF-916; Imazalil; Imazalil sulfate; Imibenconazole; Iminoctadine; Iminoctadine triacetate; Iminoctadine tris[Albesilate]; Ipconazole; Iprobenfos; Iprodione; Iprovalicarb; Kasugamycin; Kasugamycin hydrochloride hydrate; Kresoxim-methyl; Mancopper; Mancozeb; Maneb; Mepanipyrim; Mepronil; mercuric chloride; mercuric oxide; mercurous chloride; Metalaxyl; Metalaxyl-M; Metam; Metam-sodium; Metconazole; Methasulfocarb; methyl isothiocyanate; Metiram; Metominostrobin (SSF-126); MON65500; Myclotbutanil; Nabam; naphthenic acid; Natamycin; nickel bis (dimethyldithiocarbamate); Nitrothal-isopropyl; Nuarimol; Octhilinone; Ofurace; oleic acid (fatty acids); Oxadixyl; Oxine-copper; Oxycarboxin; Penconazole; Pencycuron; Pentachlorophenol; pentachlorophenyl laurate; Perfurazoate; phenylmercury acetate; *Phlebiopsis gigantea*; Phthalide; Piperalin; polyoxin B; polyoxins; Polyoxorim; potassium hydroxyquinoline sulfate; Probenazole; Prochloraz; Procymidone; Propamocarb; Propamocarb Hydrochloride; Propiconazole; Propineb; Pyrazophos; Pyributicarb; Pyrifenox; Pyrimethanil; Pyroquilon; Quinoxyfen; Quintozene; RH-7281; sec-butylamine; sodium 2-phenylphenoxide; sodium pentachlorophenoxide; Spiroxamine (KWG 4168); *Streptomyces griseoviridis*; sulfur; tar oils; Tebuconazole; Tecnazene; Tetraconazole; Thiabendazole; Thifluzamide; Thiophanate-methyl; Thiram; Tolclofos-methyl; Tolylfluanid; Triadimefon; Triadimenol; Triazoxide; *Trichoderma harzianum*; Tricyclazole; Tridemorph; Triflumizole; Triforine; Triticonzole; Validamycin; vinclozolin; zinc naphthenate; Zineb; Ziram; the compounds having the chemical name methyl (E,E)-2-(2-(1-(1-(2-pyridyl) propyloxyimino)-1-cyclopropylmethyloxymethyl)phenyl)-3-ethoxypropenoate and 3-(3,5-dichlorophenyl)-4-chloropyrazole.

Among the insecticide, acaricide and nematocide active substances which may be used alone or in combination with other active substances, in particular pesticides, in the compositions according to the invention, there may be mentioned Abamectin; Acephate; Acetamiprid; oleic acid; Acrinathrin; Aldicarb; Alanycarb; Allethrin [(1R) isomers]; α-Cypermethrin; Amitraz; Avermectin B1 and its derivatives, Azadirachtin; Azamethiphos; Azinphos-ethyl; Azinphosmethyl; *Bacillus thurigiensi*; Bendiocarb; Benfuracarb; Bensultap; β-cyfluthrin; β-cypermethrin; Bifenazate; Bifenthrin; Bioallathrin; Bioallethrin (S-cyclopentenyl isomer); Bioresmethrin; Borax; Buprofezin; Butocarboxim; Butoxycarboxim; piperonyl butoxide; Cadusafos; Carbaryl; Carbofuran; Carbosulfan; Cartap; Cartap hydrochloride; Chordane; Chlorethoxyfos; Chlorfenapyr; Chlorfenvirnphos; Chlorfluazuron; Chlormephos; Chloropicrin; Chlorpyrifos; Chlorpyrifos-methyl; mercurous chloride; Coumaphos; Cryolite; Cryomazine; Cyanophos; calcium cyanide; sodium cyanide; Cycloprothrin; Cyfluthrin; Cyhalothrin; cypermethrin; cyphenothrin [(1R) transisomers]; Dazomet; DDT; Deltamethrin; Demeton-S-methyl; Diafenthiuron; Diazinon; ethylene dibromide; ethylene dichloride; Dichlorvos; Dicofol; Dicrotophos; Diflubenzuron; Dimethoate; Dimethylvinphos; Diofenolan; Disulfoton; DNOC; DPX-JW062 and DP; Empenthrin [(EZ)-(1R) isomers]; Endosulfan; ENT 8184; EPN; Esfenvalerate; Ethiofencarb; Ethion; Ethiprole having the chemical name 5-amino-3-cyano-1-(2,6-dichloro-4-trifluoromethylphenyl)-4-ethylsulfinylpyrazole; Ethoprophos; Etofenprox; Etoxazole; Etrimfos; Famphur; Fenamiphos; Fenitrothion; Fenobucarb; Fenoxycarb; Fenpropathrin; Fenthion; Fenvalerate; Fipronil and the compounds of the arylpyrazole family; Flucycloxuron; Flucythrinate; Flufenoxuron; Flufenprox; Flumethrin; Fluofenprox; sodium fluoride; sulfuryl fluoride; Fonofos; Formetanate; Formetanate hydrochloride; Formothion; Furathiocarb; Gamma-HCH; GY-81; Halofenozide; Heptachlor; Heptenophos; Hexaflumuron; sodium hexafluorosilicate; tar oils; petroleum oils; Hydramethylnon; hydrogen cyanide; Hydroprene; Imidacloprid; Imiprothrin; Indoxacarb; Isazofos; Isofenphos; Isoprocarb; Methyl isothiocyanal; Isoxathion; lambda-Cyhalothrin; pentachlorophenyl laurate; Lufenuron; Malathion; MB-599; Mecarbam; Methacrifos; Methamidophos; Methidathion; Methiocarb; Methomyl; Methoprene; Methoxychlor; Metolcarb; Mevinphos; Milbemectin and its derivatives; Monocrotophos; Naled; nicotine; Nitenpyram; Nithiazine; Novaluron; Omethoate; Oxamyl; Oxydemeton-methyl; *Paecilomyces fumosoroseus*; Parathion; Parathion-methyl; pentachlorophenol; sodium pentachlorophenoxide; Permethrin; Penothrin [(1R)-trans-isomers]; Phenthoate; Phorate; Phosalone; Phosmet; Phosphamidon; phosphine; aluminum phosphide; magnesium phosphide; zinc phosphide; Phoxim; Pirimicarb; Pirimiphos-ethyl; Pirimiphos-methyl; calcium polysulfide; Prallethrin; Profenfos; Propaphos; Propetamphos; Propoxur; Prothiofos; Pyraclofos; pyrethrins (chrysanthemates, pyrethrates, pyrethrum; Pyretrozine; Pyridaben; Pyridaphenthion; Pyrimidifen; Pyriproxyfen; Quinalphos; Resmethrin; RH-2485; Rotenone; RU 15525; Silafluofen; Sulcofuron-sodium; Sulfotep; sulfuramide; Sulprofos; Ta-fluvalinate; Tebufenozide; Tebupirimfos; Teflubenzuron; Tefluthrin; Temephos; Terbufos; Tetrachlorvinphos; Tetramethacarb; Tetramethrin [(1R) isomers]; θ-cypermethrin; Thiametoxam; Thiocyclam; Thiocyclam hydrogen oxalate; Thiodicarb; Thiofanox; Thiometon; Tralomethrin; Transfluthrin; Triazamate; Triazophos; Trichlorfon; Triflumuron; Trimethacarb; Vamidothion; XDE-105; XMC; Xylylcarb; Zeta-cypermethrin; ZXI 8901; the compound whose chemical name is 3-acetyl-5-amino-1-[2,6-dichloro-4-(trifluoromethyl)phenyl]-2-methylsulfinylpyrazole.

Among the herbicide active substances which may be used alone or in combination with other active substances, in particular pesticides, in the compositions according to the invention, there may be mentioned 2,3,6-TBA; 2,4-D; 2,4-D-2-ethylhexyl; 2,4-DB; 2,4-DB-butyl; 2,4-DB-dimethylammonium; 2,4-DB-isooctyl; 2,4-DB-potassium; 2,4-DB-sodium; 2,4-D-butotyl (2,4-D-Butotyl (2,4-D Butoxyethyl Ester)); 2,4-D-butyl; 2,4-D-dimethylammonium; 2,4-D-Diolamine; 2,4-D-isoctyl; 2,4-D-isopropyl; 2,4-D-sodium; 2,4-D-trolamine; Acetochlor; Acifluorfen; Acifluorfen-sodium; Aclonifen; Acrolein; AKH-7088; Alachlor; Alloxydim; Alloxydim-sodium; Ametryn; Amidosulfuron; Amitrole; ammonium sulfamate; Anilofos; Asulam; Asulam-sodium; Atrazine; Azafenidin; Azimsulfuron; Benazolin; Benazolin-ethyl; Benfluralin; Benfuresate; Benoxacor; Bensulfuron; Bensulfuron-methyl; Bensulide; Bentazone; Bentazone-sodium; Benofenap; Bifenox; Bilanofos; Bilanafos-sodium; Bispyribac-sodium; Borax; Bromacil; Bromobutide; Bromofenoxim; Bromoxynil; Bromoxynil-heptanoate; Bromoxynil-octanoate; Bromoxynil-potassium, Butachlor; Butamifos; Butralin; Butroxydim; butylate; Cafenstrole; Carbetamide; Carfentrazone-ethyl; Chlomethoxyfen; Chloramben; Chlorbromuron; Chloridazon; Chlorimuron; Chlorimuron-ethyl; Chloroacetic Acid; Chlorotoluron; Chlorpropham; Chlorsulfuron; Chlorthal; Chlorthal-dimethyl; Chlorthiamid; Cinmethylin; Cinosulfuron; Clethodim; Clodinafop; Clodinafop-Propargyl; Clomazone; Clomeprop; Clopyralid; Clopyralid-Olamine; Cloquintocet; Cloquintocet-Mexyl; Chloransulam-methyl; CPA; CPA-dimethylammonium; CPA-isoctyl; CPA-thioethyl; Cyanamide; Cyanazine; Cycloate; Cyclosulfamuron; Cycloxydim; Cyhalofop-butyl; Daimuron; Dalapon; Dalapon-sodium; Dazomet; Desmeduipham; Desmetryn; Dicamba; Dicamba-dimethylammonium; Dicamba-potassium; Dicamba-sodium; Dicamba-trolamine; Dichlobenil; Dichlormid; Dichlorprop; Dichlorprop-butotyl (Dichlorprop-butotyl (Dichlorpropbutoxyethyl ester)); Dichlorprop-dimethylammonium; Dichlorprop-isoctyl; Dichlorprop-P; Dichlorprop-potassium; Diclofop; Diclofop-methyl; Difenzoquat; Difenzoquat metilsulfate; Diflufenican; Diflufenzopyr (BAS 654 00 H); Dimefuron; Dimepiperate; Dimethachlor; Dimethametryn; Dimethenamid; Dimethipin; dimethylarsinic acid; Dinitramine; Dinoterb; Dinoterb acetate; Dinoterb-ammonium; Dinoterb-diolamine; Diphenamid; Diquat; Diquat dibromide; Dithiopyr; Diuron; DNOC; DSMA; Endothal; EPTC; Esprocarb; Ethalfluralin;

Ethametsulfuron-methyl; Ethofumesate; Ethoxysulfuron; Etobenzanid; Fenchlorazole-ethyl; Fenclorim; Fenoxaprop-P; Fenoxaprop-P-ethyl; Fenuron; Fenuron-TCA; Ferrous Sulfate; Flamprop-M; Flamprop-M-Isopropyl; Flamprop-M-methyl; Flazasulfuron; Fluazifop; Fluazifop-butyl; Fluazifop-P; Fluazifop-P-butyl; Fluazolate; Fluchloralin; Flufenacet (BAS FOE 5043); Flumetsulam; Flumiclorac; Flumiclorac-Pentyl; Flumioxazin; Fluometuron; Fluoroglycofen; Fluroglycofen-ethyl; Flupaxam; Flupoxam; Flupropanate; Flupropanate-sodium; Flupyrsulfuron-methyl-sodium; Flurazole; Flurenol; Flurenol-butyl; Fluridone; Flurochloridone; Fluroxypyr; Fluroxypyr-2-Butoxy-1-methylethyl; Fluroxypyr-methyl; Flurtamone; Fluthioacet-methyl; Fluxofenim; Fomesafen; Fomesafen-sodium; Fosamine; Fosamine-ammonium; Furilazole; Glyphosate; Glufosinate; Glufosinate-ammonium; Glyphosate-ammonium; Glyphosate-isopropylammonium; Glyphosate-sodium; Glyphosate-trimesium; Halosulfuron; Halosulfuron-methyl; Haloxyfop; Haloxyfop-P-methyl; Haloxyfop-etotyl; Haloxyfop-methyl; Hexazinone; Hilanafos; Imazacluin; Imazamethabenz; Imazamox; Imazapyr; Imazapyr-isopropylammonium; Imazaquin; Imazaquin-ammonium; Imazemethabenz-methyl; Imazethapyr; Imazethapyr-ammonium; Imazosulfuron; Imizapic (AC 263,222); Indanofan; Ioxynil; Ioxynil octanoate; Ioxynil-sodium; Isoproturon; Isouron; Isoxaben; Isoxaflutole; Lactofen; Laxynel octanoate; Laxynil-sodium; Lenacil; Linuron; MCPA; MCPA-butotyl; MCPA-dimethylammonium; MCPA-isoctyl; MCPA-potassium; MCPA-sodium; MCPA-thioethyl; MCPB; MCPB-ethyl; MCPB-sodium; Mecoprop; Mecoprop-P; Mefenacet; Mefenpyr-diethyl; Mefluidide; Mesulfuron-methyl; Metam; Metamitron; Metam-sodium; Metezachlor; Methabenzthiazuron; methyl isothiocyanate; methylarsonic acid; Methyldymron; Metobenzuron; Metobromuron; Metolachlor; Metosulam; Metoxuron; Metribuzin; Metsulfuron; Molinate; Monolinuron; MPB-sodium; MSMA; Napropamide; Naptalam; Naptalam-sodium; Neburon; Nicosulfuron; nonanoic acid; Norflurazon; oleic acid (fatty acids); Orbencarb; Oryzalin; Oxabetrinil; Oxadiargyl; Oxasulfuron; Oxodiazon; Oxyfluorfen; Paraquat; Paraquat Dichloride; Pebulate; Pendimethalin; Pentachlorophenol; Pentachlorophenyl Laurate; Pentanochlor; Pentoxazone; petroleum oils; Phenmedipham; Picloram; Picloram-potassium; Piperophos; Pretilachlor; Primisulfuron; Primisulfuron-methyl; Prodiamine; Prometon; Prometryn; Propachlor; Propanil; Propaquizafop; Propazine; Propham; Propisochlor; Propyzamide; Prosulfocarb; Prosulfuron; Pyraflufen-ethyl; Pyrazasulfuron; Pyrazolynate; Pyrazosulfuron-ethyl; Pyrazoxyfen; Pyribenzoxim; Pyributicarb; Pyridate; Pyriminobac-methyl; Pyrithiobac-sodium; Quinclorac; Quinmerac; Quinofolamine; Quizalofop; Quizalofop-ethyl; Quizalofop-P; Quizalofop-P-ethyl; Quizalofop-P-Tefuryl; Rimsulfuron; Sethoxydim; Siduron; Simazine; Simetryn; sodium chlorate; sodium chloroacetate; sodium pentachlorophenoxide; sodium-Dimethylarsinate; Sulcotrione; Sulfentrazone; Sulfometuron; Sulfometuron-methyl; Sulfosulfuron; Sulfuric acid; tars; TCA-sodium; Tebutam; Tebuthiuron; Tepraluxydim (BAS 620H); Terbacil; Terbumeton; Terbuthylazine; Terbutryn; Thenylchlor; Thiazopyr; Thifensulfuron; Thifensulfuron-methyl; Thiobencarb; Tiocarbazil; Tralkoxydim; triallate; Triasulfuron; Triaziflam; Tribenuron; Tribenuron-methyl; Tribenuron-methyl; trichloroacetic acid; Triclopyr; Triclopyr-butotyl; Triclopyr-triethylammonium; Trietazine; Trifluralin; Triflusulfuron; Triflusulfuron-methyl; Vernolate: YRC 2388.

In the compositions according to the invention, the active substance(s) may be provided in various physical forms, in particular in solid form, or in liquid or semiliquid form.

The active substance(s) of the compositions according to the invention is (are) provided in quantities of between 0.5 and 99.99%, preferably between 5 and 70% by weight of said compositions.

The dendrimers used in the compositions according to the invention, also called dendrimers according to the invention, are dendrimers capable of forming a gel.

An advantageous method for knowing if a particular dendrimer is capable of forming a gel consists in mixing, at a temperature of about 65° C., said dendrimer with water in the respective proportions by weight of 1.5/98.5; the mixture forms a gel within the meaning of the present invention if, after 48 hours, the product obtained does not flow when it is placed, in the form of a cubic mass, on a flat surface.

According to another method which makes it possible to know if a particular dendrimer is capable of forming a gel of high quality which is particularly advantageous for the invention, said dendrimer is mixed, at room temperature, with water in the respective proportions by weight of 1/1; the mixture forms a gel within the meaning of the present invention if, after two weeks, the product obtained does not flow when it is placed, in the form of a cubic mass, on a flat surface.

Another particularly advantageous method for determining if a particular dendrimer is capable of forming a gel may consist in proceeding as follows: the particular dendrimer is mixed with water, preferably solubilized in water, in the respective proportions by weight of 1.8/98.2, at a temperature which may be between 40 and 65° C., and then this mixture is heated for 4 weeks at a temperature of about 60–65° C., to give a gelled product which does not flow when it is placed, in the form of a cubic mass, on a flat surface.

According to another aspect of the invention, the gels which are capable of being formed by the particular dendrimer useful for the composition according to the invention are colloids with a substantially continuous phase and which give a jelly type viscous product; this may also include a dispersed system consisting, for example, of a high-molecular weight compound or an aggregate of molecules of dendrimers useful for the compositions according to the invention, in intimate association with an inorganic or organic liquid carrier.

According to a preferred variant of the invention, the gels which the dendrimers for the invention are capable of forming have a Brookfield-type viscosity of between 400 and 10,000 centipoises, more preferably between 800 and 5,000 centipoises.

The dendrimers according to the invention and which are therefore the dendrimers capable of forming a gel may be in particular neutral dendrimers or dendrimers of the ionic type, either of the anionic or cationic type.

As dendrimers useful according to the invention which are neutral, there may be mentioned those whose terminal functional groups mainly consist of groups of the carboxylic acid type and/or of the phosphonic type and/or of the sulfonic, sulfonate or sulfate type and/or of the amine type.

As dendrimers useful according to the invention and which are of the ionic type, there may be advantageously mentioned the dendrimers whose terminal functional groups essentially comprise groups chosen from carboxylate and/or sulfonium and/or phosphonium and/or amidinium and/or guanidinium and/or ammonium groups, for example groups of the secondary, tertiary or quaternary ammonium type, most particularly groups of the pyridinium type.

As dendrimers useful for the compositions according to the invention and which are most particularly advantageous, there may be mentioned particular dendrimers whose terminal functional groups essentially comprise radicals derived from groups of the N-hydrazinoylcarbonylmethyl-N,N,N-trialkylammonium halide type, among which groups there may be mentioned, by way of example, N-hydrazinoylcarbonylmethyl-N,N-N-tri-(n-propyl) ammonium chloride called Girard PR reagent or N-hydrazinoylcarbonylmethyl-N,N,N-trimethylammonium chloride represented by FIG. (V) below and which will be called Girard T reagent for the remainder of the present text; likewise there may be mentioned N-hydrazinoylcarbonylmethyl-N,N,N-pyridinium chloride called Girard P reagent for the remainder of the present text.

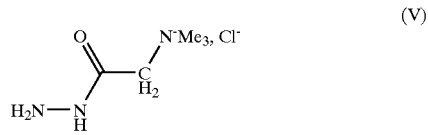

(V)

Said terminal functional groups of the dendrimers according to the invention are attached to the ends of the branched chains which the branches of said dendrimers constitute, either directly or by means of an organic chemical reagent called connecting member for the present disclosure.

Said connecting member of the dendrimers of the invention is most often composed of a hydrocarbon radical containing from 2 to 50 carbon atoms, preferably from 4 to 20 carbon atoms, it being possible for said radical to be saturated or unsaturated and/or linear or branched and/or substituted or unsubstituted.

Said connecting member may also be composed of a hydrocarbon radical as defined above and containing, in addition to carbon atoms, one or more heteroatoms, in particular oxygen, sulfur, nitrogen, phosphorus or halogens.

As connecting members useful for the dendrimers used in the compositions according to the invention, there may be mentioned groups of the type including alkyl, aryl, alkoxyalkyl, alkoxyaryl, alkylhydrazinoyl, arylhydrazinoyl, carboxyalkyl-hydrazido and in particular carboxymethyl-hydrazido, cyanoalkyl, allyl, propargyl, halocycloalkyl, haloalkoxyalkyl, alkylthioalkyl, haloalkylthioalkyl, aminoalkyl, N-alkylaminoalkyl, N,N-dialkylaminoalkyl, acylaminoalkyl, arylalkyl, phenyliminoalkyl, iminoaryl, imidoalkyl, amidoaryl, phosphoalkyl, phosphoryl, thiophosphoryl, phosphoraminoalkyl, phosphoraminoaryl, phosphoriminoalkyl, phosphoriminoaryl, phosphorimidoalkyl, phosphorimidoaryl, hydrazinoalkyl, hydrazinoaryl, allylidenealkylhydrazynoyl, allylidenearylhydrazinoyl, epoxybenzylidene, dialkylphosporimidoyl, diarylphosphorimidoyl, thioimidophosphoryl, thio-N-alkylazophosphoryl, thio-N-arylazophosphoryl optionally substituted with one or more groups chosen from the groups of the type including hydroxyl, mercapto, nitro, thiocyanate, azido, cyano, pentafluorosulfonyl, alkyl, aryl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl and alkoxysulfonyl, cycloalkyl, alkenyl, alkynyl, alkenyloxy, alkynyloxy, alkenylthio, alkynylthio, amino, N-alkylamino, N,N-dialkylamino, acylamino, hydroxy, alkoxy, carboxy, carbamoyl, N-alkylcarbamoyl, N,N-dialkylcarbamoyl, alkoxycarbonyl, acyl.

Preferably, the dendrimers used in the compositions according to the invention carry bonds between atoms from group V A of the periodic table of chemical elements, said group having nitrogen as the first element and bismuth as the last element. i.e., nitrogen, phosphorus, arsenic, antimony, and bismuth. More preferably, said dendrimers carry bonds between phosphorus atoms and nitrogen atoms.

These bonds between atoms from group V A of the periodic table of chemical elements may be present in the dendrimers useful for the compositions according to the invention in quantities ranging from a few units to several thousands, or even several tens of thousands because of the large size which said dendrimers may have, for example the number of said bonds may be between 2 and 80,000, preferably between 20 and 20,000.

As defined above, the organic core of the dendrimers useful for the compositions according to the invention most often consists of a polyfunctional organic chemical group capable of being attached to multiple branched chains.

Said core may also be characterized by a multiple valency which corresponds to the number of dendrons to which it is capable of being directly attached so as to form a so-called first generation dendrimer.

Preferably, the core of the dendrimers according to the invention possesses a valency of between 2 and 20, preferably of between 3 and 10. Thus, the so-called first generation dendrimers according to the invention may be attached to a number of dendrons which may be up to 20, preferably up to 10.

Most often, the core of the dendrimers according to the invention is composed of a radical or of a chemical group which is complex to a greater or lesser degree; this may include a hydrocarbon radical in general containing from 1 to 30 atoms and said hydrocarbon radical may be linear, branched or cyclic or even polycyclic and/or saturated or unsaturated and/or substituted or unsubstituted.

The core of the dendrimers used in compositions according to the invention is usually composed of a hydrocarbon radical containing one or more heteroatoms, in particular oxygen, sulfur, nitrogen, phosphorus or halogens, in particular chlorine. Where appropriate and in the preferred manner, the core of the dendrimers according to the invention contains up to 100%, as number of atoms, of said heteroatoms.

As examples of compounds which are precursors of heteroatom radicals useful as core for the dendrimers according to the invention, there may be mentioned hexachlorocyclotriphosphazene or trichlorothiophosphane; a representation of the chemical structure of these two compounds is given below by FIGS. (VI) and (VII).

The expression precursor compounds is understood to mean compounds which may precede the formation or the preparation of radicals useful as core for the dendrimers according to the invention.

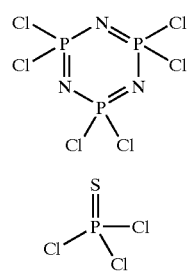

(VI)

(VII)

As defined above, the branches or dendrons of the dendrimers according to the invention most often consist of branched organic chains linked to the core of said dendrimers.

Said branched organic chains are usually composed of hydrocarbon radicals which are complex to a greater or lesser degree, said hydrocarbon radicals may also comprise a number of heteroatoms such as oxygen, sulfur, nitrogen, phosphorus or halogens, in particular chlorine.

In general, said dendrons are series of said branched chains; in other words, the dendrimers according to the invention most often possess dendrons which are composed of branched chains containing chemical motifs which are in part identical or similar to each other.

As the dendrimers according to the invention may possess a large number of dendrons, the number of said identical or similar chemical motifs is highly variable. Usually, the dendrimers according to the invention possess dendrons which are composed of series of branched chains containing chemical motifs among which 10%, preferably 20%, of the total number of chemical motifs are identical or similar to each other. In other words, the dendrons of the dendrimers according to the invention may be composed of chemical units of which 9/10, preferably 4/5, are different from each other.

Said chemical motifs which compose the dendrons of the dendrimers used for the compositions according to the invention may, for example, be chosen from the groups of the type including alkyl, aryl, alkoxyalkyl, alkoxyaryl, alkylhydrazinoyl, arylhydrazinoyl, carboxyalkyl-hydrazido and in particular carboxymethyl-hydrazido, cyanoalkyl, allyl, propargyl, halocycloalkyl, haloalkoxyalkyl, alkylthioalkyl, haloalkylthioalkyl, aminoalkyl, N-alkylaminoalkyl, N,N-dialkylaminoalkyl, acylaminoalkyl, arylalkyl, phenyliminoalkyl, iminoaryl, imidoalkyl, amidoaryl, phosphoalkyl, phosphoryl, thiophosphoryl, phosphoraminoalkyl, phosphoraminoaryl, phosphoriminoalkyl, phosphoriminoaryl, phosphorimidoalkyl, phosphorimidoaryl, hydrazinoalkyl, hydrazinoaryl, allylidenealkylhydrazynoyl, allylidenearylhydrazinoyl, epoxybenzylidene, dialkylphosporimidoyl, diarylphosphorimidoyl, thioimidophosphoryl, thio-N-alkylazophosphoryl, thio-N-arylazophosphoryl optionally substituted with one or more groups chosen from the groups of the type including hydroxyl, mercapto, nitro, thiocyanate, azido, cyano, pentafluorosulfonyl, alkyl, aryl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl and alkoxysulfonyl, cycloalkyl, alkenyl, alkynyl, alkenyloxy, alkynyloxy, alkenylthio, alkynylthio, amino, N-alkylamino, N,N-dialkylamino, acylamino, hydroxy, alkoxy, carboxy, carbamoyl, N-alkylcarbamoyl, N,N-dialkylcarbamoyl, alkoxycarbonyl, acyl.

In addition to the core, the dendrons and the terminal functional groups, the dendrimers used in compositions according to the invention comprise inner cavities inherently resulting from the existence of branches characteristic of the spatial structure of said dendrimers.

Said inner cavities may in particular allow the inclusion of a variety of substances within the arborescent structure of said dendrimers. However, the size and the accessibility of these inner cavities limits the inclusion of said substances to only molecules whose size and properties are compatible therewith.

By way of purely illustrative example, FIG. (VIII) below gives a representation of such a dendrimer.

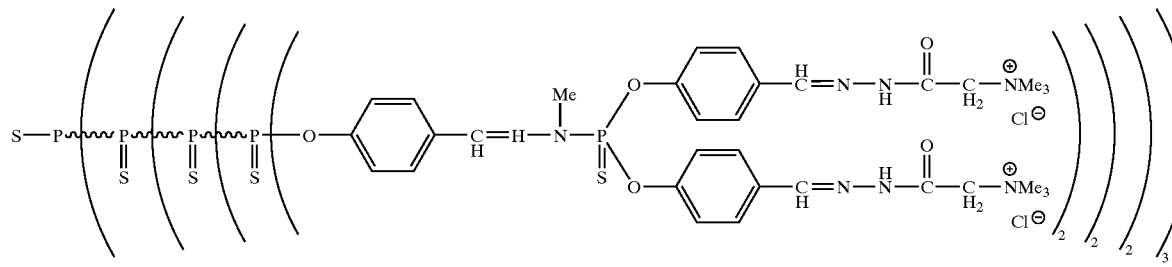

(VIII)

Moreover and by virtue of the variety and number of terminal functional groups which the dendrimers used in the compositions according to the invention may comprise, said dendrimers may be described as being multiplurifunctionalized.

Thus, multiplurifunctionalized describes a dendrimer used in the compositions according to the invention which carries, at its periphery, several terminal functional groups of different chemical types, hence the prefix pluri, and in which the plurality of said chemical functional groups is repeated because of the multiple functional groups of said dendrimer, hence the prefix multi.

A symbolic representation of such a multiplurifunctionalized, more precisely multitetrafunctionalized, dendrimer which may be used in the compositions according to the invention is given below by FIG. (IX) in which the symbols ○, ●, * and # represent terminal functional groups of four different chemical types and the broken lines represent the dendrons of the dendrimer represented.

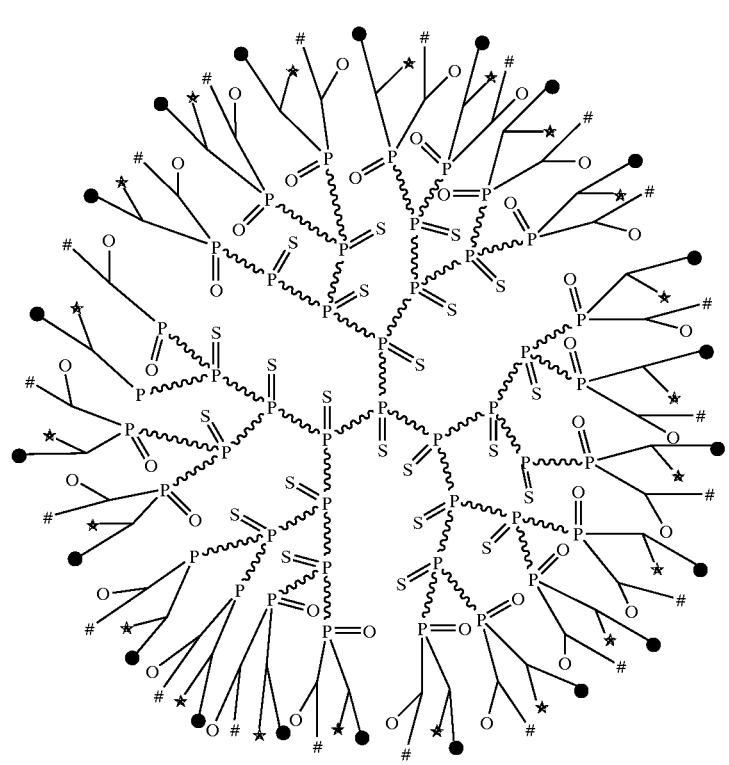

(IX)

The gels formed by the dendrimers useful for the compositions according to the invention have the characteristic feature of being able to comprise, in their structure, volumes for insertion, for example of active substance, of two types:
 the inner cavities characteristic of the branched structure of the dendrimers themselves;
 the so-called interstitial spaces derived from the three-dimensional structure of said gels which said dendrimers can form.

In other words, the inner cavities are in the dendrimers used in the compositions according to the invention while the interstitial spaces are outside the arborescent structure of said dendrimers.

Said inner cavities of the dendrimers according to the invention have sizes generally of between 0.001 and 30 nm$^3$, preferably between 0.01 and 10 nm$^3$. The unit of measurement which makes it possible to assess the size of these volumes corresponds to the volume of a cube 1 nm (nanometer) along the side.

The so-called interstitial spaces of the gels which the dendrimers useful for the compositions according to the invention may form have sizes in general of between 0.0005 and 50 $\mu$m$^3$, preferably between 0.001 and 20 $\mu$m$^3$. The unit of measurement which makes it possible to assess the size of these volumes corresponds to the volume of a cube 1 $\mu$m (micrometer or micron) along the side.

The dendrimers used in compositions according to the invention are generally contained in compositions according to the invention in quantities of between 0.01 and 99.5%, preferably between 0.1 and 60%, by weight of said compositions.

The invention further relates to compositions which can be used in the fields of agriculture and/or public health or domestic hygiene and which contain dendrimers according to the invention and one or more active substances located as a whole or in part in the interstitial spaces of said dendrimers and, for the remainder, integrated into the inner cavities of said dendrimers.

The compositions according to the invention which are particularly advantageous are those in which at least half of the active substance is contained in the interstitial spaces of the gels formed by the dendrimers according to the invention.

This characteristic of the compositions according to the invention of being able to integrate part of the active substance into the said interstitial spaces, that is to say into the structure of the gels which the dendrimers used may form, is particularly advantageous when the size of said active substance make its location within the inner cavities of said dendrimers difficult or even impossible.

The invention therefore relates to compositions as described above, but also compositions according to the invention comprising several active substances, in particular several active substances which can be used in the fields of agriculture and/or public health or domestic hygiene, in particular several pesticide active substances and/or several insecticide and/or plant growth regulating active substances.

The compositions according to the invention associating or combining several of said active substances are of special interest when said compositions allow the use of several active substances possessing complementary activity spectra or when said active substances possess properties such that their association or combination may allow substantial improvement in the respective action of each of these active substances or may allow a reduction in the respective quantity of each active substance used, the latter quality being particularly important for easily understandable ecological reasons.

Thus, a most special advantage of the compositions according to the invention may consist in the possibility of associating or combining several active substances, in particular in the possibility of associating or combining one or more substances of the type including insecticides and/or acaricides and/or rodenticides and/or nematocides and/or insects and/or animal pest repellents with one or more attractants for said insects or animal pests.

In addition to one or more active substances as defined above and one or more dendrimers capable of forming a gel, the compositions according to the invention comprise an inorganic or organic liquid carrier.

For the disclosure of the present invention, the expression inorganic or organic liquid carrier is most often understood to mean both a solvent used alone and an association of several solvents. Such an association then consisting of a solvent and one or more co-solvents miscible with each other or not.

As solvents used in the compositions according to the invention, water and/or organic solvents may be used.

When water is used as solvent in the compositions according to the invention, the values of its pH may either correspond to a basic medium or to an acidic medium, for example depending on the type of dendrimer used.

The organic solvents optionally used for the compositions used according to the invention are protic or aprotic organic solvents.

Among the organic solvents used for the compositions according to the invention, polar organic solvents are preferred, said organic solvents are advantageously chosen from glycerol, ethanol, acetonitrile, tetrahydrofuran, dimethyl sulfoxide, N-methylpyrrolidone or cyclohexanone.

For the compositions according to the invention, the quantity of solvent may vary from 0 to 99% by weight of said compositions.

For the compositions according to the invention which use a solvent and one or more co-solvents, the relative quantities of these so-called solvents and co-solvents vary in proportions of the solvent/co-solvent ratio ranging from 95/5 to 50/50.

According to a particularly advantageous embodiment, the compositions according to the invention are capable of releasing gradually and/or in a controlled manner all or some of the active substance usable in particular in the fields of agriculture and/or public health or domestic hygiene which they contain.

Very advantageously, these compositions according to the invention are capable of releasing at least 50%, preferably at least 80%, of the active substance usable in particular in the fields of agriculture and/or public health or domestic hygiene which they contain.

Preparation of the Compositions According to the Invention

The present invention also relates to the methods for preparing the compositions according to the invention.

The methods for preparing and formulating the compositions according to the invention most often make use of customary formulation techniques; however, by way of example and to allow better illustration of the present invention, a method for preparing compositions according to the invention is given below.

Unless otherwise stated, the quantities of the various constituents used during said preparations are expressed as percentage by weight of composition prepared.

Thus, to prepare said compositions, the procedure begins by mixing with the solvent, or with the solvent/co-solvent(s) mixture, the dendrimer(s) capable of forming a gel in a quantity which is most often between 0.01 and 99.5%, preferably between 0.1 and 60%. Next, the active substance(s) is(are) added to the mixture thus prepared in quantities of between 0.5 and 99.99%, preferably between 5 and 70%. The formulation additives and adjuvants optionally used in the compositions according to the invention may be added during any of the steps previously described; persons skilled in the art will know how to determine the most appropriate step and the useful quantities of said additives and adjuvants, said quantities being advantageously between 0 and 50%. After storing for a period which is most often between a few hours and a few weeks, at a temperature in general between room temperature and about 80° C., preferably between 30 and 70° C., the mixture thus prepared makes it possible to obtain the compositions according to the invention.

According to another mode of preparation of a composition according to the invention, the procedure is carried out as follows: mixing or solubilization, preferably in the hot state, of one or more active substances usable in the fields of agriculture and/or public health or domestic hygiene, of one or more dendrimers capable of forming a gel and an inorganic or organic liquid carrier, and then heating said mixture for 0.25 to 45 days, at a temperature of about 60–65° C., preferably at a temperature of about 35–40° C.

Pulverulent Compositions Useful in the Fields of Agriculture and/or Public Health or Domestic Hygiene Another aspect of the present invention relates to pulverulent compositions usable in the fields of agriculture and/or public health or domestic hygiene and which, mixed with an inorganic or organic liquid carrier or solvent, are capable of taking the shape of compositions in gelled form, said compositions in gelled form being of the type including those described above in the present text.

The pulverulent compositions according to the invention may be obtained by complete or partial removal of the solvent(s) from the compositions in gelled form according to the invention which are described above and containing, in addition to the solvent(s), one or more pesticide and/or insecticide and/or plant growth regulating active substances, a dendrimer according to the invention capable of forming a gel and, optionally, one or more formulation adjuvants and/or additives.

Thus, said pulverulent compositions according to the invention may, for example, contain anticaking agents, colorants, thickeners, surfactants, antifoaming compounds, detergents such as alkaline-earth metal salts, dispersants, alkalinizing agents such as bases, bonding agents, emulsifiers, oxidizing agents such as free radical scavengers or catalytic destroyers of hydroperoxides, anticorrosive agents, attractants and/or food substances for the preparation of insecticide baits in particular.

More generally, the pulverent compositions according to the invention may comprise any solid or liquid additives corresponding to the formulation techniques which are acceptable for uses in the fields of agriculture and/or public health or domestic hygiene for example.

The active substances used in the pulverulent compositions according to the invention are the active substances used for the formulation of compositions in gelled form according to the invention and previously described in detail in the present text. Thus, among said active substances used in the pulverulent compositions according to the invention, there may be mentioned all those which were previously cited as examples of active substances which the compositions in gelled form according to the invention may contain.

The active substance(s) of the pulverulent compositions according to the invention is (are) present in quantities of between 2 and 99.99%, preferably between 5 and 95% by weight of said pulverulent compositions.

Likewise, the dendrimers used in the pulverulent compositions according to the invention are the dendrimers used for the compositions in gelled form according to the invention and previously described.

In general, the principal characteristic of said dendrimers is being capable of forming a gel as described above and thus conferring on the pulverulent compositions according to the invention their essential property of allowing the reconstitution of the compositions in gelled form according to the invention.

The dendrimer(s) useful for the pulverulent compositions according to the invention may be present in said pulverulent compositions in quantities of between 0.01 and 99.5%, preferably between 0.5 and 50%, by weight of said pulverulent compositions.

It has therefore been discovered that the compositions in gelled form according to the invention may be freed of all or part of the solvent(s) which they contain, thus allowing the preparation of the pulverulent compositions according to the invention.

As techniques used for the preparation of said pulverulent compositions according to the invention, freeze-drying or spray-drying may be mentioned.

The aim of freeze-drying is to obtain pulverulent compositions according to the invention which are solid, brittle, have a porous appearance, and are essentially characterized by a very high affinity for the solvent(s) which may be used during the reconstitution, from said pulverulent compositions, of the compositions in gelled form according to the invention.

Freeze-drying consists in extracting the solvent(s) contained in the compositions in gelled form according to the invention, through the interaction of vacuum and refrigeration technologies. Indeed, a freeze-drying cycle may comprise several phases, in particular a preliminary phase for freezing the composition to be freeze-dried, followed by a phase for removing the solvent(s).

Spray-drying of the compositions in gelled form according to the invention may be carried out in a customary manner in any known apparatus such as, for example, a spray-drying tower combining spraying of said composition in gelled form and carried out by a nozzle or a turbine, with a hot gas stream.

The conditions for implementation generally depend on the nature of the solvent(s) to be removed and/or the nature of the dendrimer(s) according to the invention used and/or the heat-sensitivity of the active substance(s) used as well as the spray-dryer used; these conditions are generally such that the temperature of the whole composition according to the invention during drying does not exceed 150° C., preferably does not exceed 110° C.

The pulverulent compositions according to the invention are particularly advantageous in that, on mixing with one or more appropriate solvents, they can allow the recomposition of compositions in gelled form according to the invention.

Advantageously, the solvent(s) used for mixing with the pulverulent compositions according to the invention may be chosen from water and/or organic solvents.

When water is used as solvent added to the pulverulent compositions according to the invention, the values of its pH may either correspond to a basic medium or may correspond to an acidic medium, for example depending on the type of dendrimer used.

The organic solvents optionally added to the pulverulent compositions according to the invention are protic or aprotic organic solvents.

Among the organic solvents optionally added to the pulverulent compositions according to the invention, polar organic solvents are preferred, said organic solvents being advantageously chosen from glycerol, ethanol, acetonitrile, tetrahydrofuran, dimethyl sulfoxide, N-methylpyrrolidone or cyclohexanone.

In addition to the possibility of being able to allow the recomposition of compositions in gelled form according to the invention, the pulverulent compositions according to the invention are particularly advantageous in that they can be stored for long periods and in the absence of any precaution, this being without substantial impairment of their characteristics.

According to another advantageous embodiment, the pulverulent compositions according to the invention may be subjected to grinding in order to obtain a particle size distribution or a particle size which are appropriate for the use envisaged, in particular in order to facilitate land spraying or to enhance the biological efficacy.

Moreover, said pulverulent compositions according to the invention may also be incorporated or used in numerous types of formulations. Said formulations may be in particular in liquid form or in solid form: thus, among said formulations, there may be mentioned those of the type including aerosol dispenser; bait (ready-for-use); bait concentrate; stock bait; capsule suspension; cold fogging product; dusting powder; emulsifiable concentrate; oil-in-water emulsion; water-in-oil emulsion; encapsulated granule; fine granule; suspension concentrate for seed treatment; gas; gas generating product; grain bait; granular bait; granule; hot fogging product; macrogranule; microgranule; oil-dispersible powder; oil miscible suspension concentrate; oil miscible liquid; paste; plant rodlet; plate bait; powder for dry seed treatment; scrap bait; treated or coated seeds; smoke candle; smoke cartridge; smoke generator; smoke pellet; smoke rodlet; smoke tablet; smoke tin; soluble concentrate; soluble powder; liquid for seed treatment; suspension concentrate (=flowable concentrate); tracking powder; ultra low volume liquid; ultra low volume suspension; vapor releasing product; water dispersible granules or tablets; water dispersible powder for slurry treatment; water soluble granules or tablets; water soluble powder for seed treatment; wettable powder.

According to another embodiment, the pulverulent compositions according to the invention are capable of being obtained by drying and then cutting, grinding, disintegrating, mincing of gelled compositions according to the invention.

According to other advantageous embodiments, the pulverulent compositions according to the invention may take the form of pastilles, lumps, aggregates of variable size depending on the use considered, or crystals which can all be used as they are, in particular for land spraying, dispersion or other appropriate forms of application.

According to an embodiment which is also particularly advantageous, the pulverulent compositions according to the invention are capable of releasing gradually and/or in a controlled manner all or some of the active substance which can be used in particular in the fields of agriculture and/or public health or domestic hygiene which they contain.

More advantageously still, these pulverulent compositions according to the invention are capable of releasing at least 50%, preferably at least 80%, of the active substance which can be used in particular in the fields of agriculture and/or public health or domestic hygiene which they contain.

Novel Dendrimers

Among the dendrimers which are capable of forming a gel and which can be used in the compositions according to the invention, a particularly advantageous family comprises novel dendrimers which constitute an additional aspect of the present invention. For the remainder of the present disclosure, these novel dendrimers will be termed dendrimers which are the subject of the invention.

The gels which are capable of being formed by the dendrimers which are the subject of the invention are colloids having a substantially continuous phase and which give a viscous product of the jelly type; this may also include a dispersed system comprising, for example, a compound having a high molecular weight or an aggregate of molecules of dendrimers which are the subject of the invention, in intimate association with a liquid.

According to a preferred variant of the invention, the gels which the dendrimers which are the subject of the invention are capable of forming have a Brookfield type viscosity of between 400 and 10 000 centipoises, more particularly of between 800 and 5 000 centipoises.

As has already been mentioned above in the present disclosure, the dendrimers which are the subject of the invention are macromolecules consisting of a central part, the core, to which series of branched chains, the dendrons, are linked.

Said dendrimers most often possess an arborescent structure, said structure comprising
  a core, in general consisting of a polyfunctional chemical group capable of being linked to a plurality of branched chains;
  branches, generally composed of linear or branched organic fragments, linked to each other and to the core, and organized in an arborescent manner;
  terminal chemical functional groups, that is to say constituting the peripheral end of the branches;
  inner cavities inherently resulting from branchings of said branches.

The organic core is therefore the central part of the dendrimers which are the subject of the invention. It generally consists of a chemical group, most often an organic and polyfunctional group capable of being attached to multiple branched chains.

The core of the dendrimers which are the subject of the invention is also characterized by a multiple valency which corresponds to a number of dendrons to which it is capable of being attached.

As defined above, the organic core of the dendrimers which are the subject of the invention most often consists of a polyfunctional organic chemical group capable of being attached to multiple branched chains.

Said core may also be characterized by a multiple valency which corresponds to the number of dendrons to which it is capable of being directly attached so as to form a so-called first generation dendrimer.

Preferably, the core of the dendrimers which are the subject of the invention possesses a valency of between 2 and 20, preferably of between 3 and 10. Thus, the so-called first generation dendrimers which are the subject of the invention may be attached to a number of dendrons which may be up to 20, preferably up to 10.

Most often, the core of the dendrimers according to the invention is composed of a radical or of a chemical group which is complex to a greater or lesser degree; this may include a hydrocarbon radical in general containing from 1 to 30 atoms and said hydrocarbon radical may be linear, branched or cyclic or even polycyclic and/or saturated or unsaturated and/or substituted or otherwise.

The core of the dendrimers which are the subject of the invention is usually composed of a hydrocarbon radical containing one or more heteroatoms, in particular oxygen, sulfur, nitrogen, phosphorus or halogens, in particular chlorine. Where appropriate and in the preferred manner, the core of the dendrimers according to the invention contains up to 100%, as number of atoms, of said heteroatoms.

As examples of compounds which are precursors of heteroatom radicals useful as core for the dendrimers which are the subject of the invention, there may be mentioned hexachlorocyclotriphosphazene or trichlorothiophosphane; a representation of the chemical structure of these two compounds is given below by FIGS. (VI) and (VII).

The expression precursor compounds is understood to mean compounds which may precede the formation or the preparation of radicals useful as core of the dendrimers which are the subject of the invention.

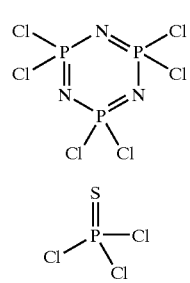 (VI)

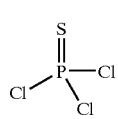 (VII)

The dendrons of the dendrimers which are the subject of the invention are branched organic chains linked to the core. Generally, said dendrons are series of said branched chains.

Said branched chains are usually composed of hydrocarbon radicals which are complex to a greater or lesser degree, said hydrocarbon radicals may also comprise a number of heteroatoms such as oxygen, sulfur, nitrogen, phosphorus or halogens, in particular chlorine.

In general, said dendrons are series of said branched chains, in other words, the dendrimers which are the subject of the invention most often possess dendrons which are composed of branched chains containing chemical motifs which are in part identical or similar to each other.

As the dendrimers which are the subject of the invention may possess a large number of dendrons, the number of said identical or similar chemical motifs is highly variable. Usually, the dendrimers which are the subject of the invention possess dendrons which are composed of series of branched chains containing chemical motifs among which 10%, preferably 20%, of the total number of said chemical motifs are identical or similar. In other words, the dendrons of the dendrimers which are the subject of the invention may be composed most often of chemical units of which 9/10, preferably 4/5, are different from each other.

Said chemical motifs which compose the dendrons of the dendrimers which are the subject of the invention may, most often, be chosen from the groups of the type including alkyl, aryl, alkoxyalkyl, alkoxyaryl, alkylhydrazinoyl, arylhydrazinoyl, carboxyalkyl-hydrazido and in particular carboxymethyl-hydrazido, cyanoalkyl, allyl, propargyl, halocycloalkyl, haloalkoxyalkyl, alkylthioalkyl, haloalkylthioalkyl, aminoalkyl, N-alkylaminoalkyl, N,N-dialkylaminoalkyl, acylaminoalkyl, arylalkyl, phenyliminoalkyl, iminoaryl, imidoalkyl, amidoaryl, phosphoalkyl, phosphoryl, thiophosphoryl, phosphoraminoalkyl, phosphoraminoaryl, phosphoriminoalkyl, phosphoriminoaryl, phosphorimidoalkyl, phosphorimidoaryl, hydrazinoalkyl, hydrazinoaryl, allylidenealkylhydrazynoyl, allylidenearylhydrazinoyl, epoxybenzylidene, dialkylphosporimidoyl, diarylphosphorimidoyl, thioimidophosphoryl, thio-N-alkylazophosphoryl, thio-N-arylazophosphoryl optionally substituted with one or more groups chosen from the groups of the type including hydroxyl, mercapto, nitro, thiocyanate, azido, cyano, pentafluorosulfonyl, alkyl, aryl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl and alkoxysulfonyl, cycloalkyl, alkenyl, alkynyl, alkenyloxy, alkynyloxy, alkenylthio, alkynylthio, amino, N-alkylamino, N,N-dialkylamino, acylamino, hydroxy, alkoxy, carboxy, carbamoyl, N-alkylcarbamoyl, N,N-dialkylcarbamoyl, alkoxycarbonyl, acyl.

The terminal functional groups of the dendrimers which are the subject of the invention are chemical functional groups present at the ends of said dendrons; among the very many chemical functional groups which may constitute said terminal functional groups, there may be mentioned, for example, the ammonium, amidinium, pyridinium, guanidinium or carboxylate functional groups or carboxylic acids. Said terminal functional groups usually confer on the dendrimers which are the subject of the invention, some of their characteristics, in particular the possibility of very many individual reactions at the periphery.

The terminal functional groups of the dendrimers which are the subject of the invention are attached to the ends of the branched chains which the branches of said dendrimers constitute, either directly or by means of an organic chemical residue called connecting member for the present disclosure.

Said connecting member of the dendrimers which are the subject of the invention is most often composed of a hydrocarbon radical containing from 2 to 50 carbon atoms, preferably from 4 to 20 carbon atoms, it being possible for said radical to be saturated or unsaturated and/or linear or branched and/or substituted or otherwise.

Said connecting member may also be composed of a hydrocarbon radical as defined above and containing, in addition to carbon atoms, one or more heteroatoms, in particular oxygen, sulfur, nitrogen, phosphorus, halogens or any other element useful for conferring on the dendrimers which are the subject of the invention properties characterizing them, in particular their chemical reactivity.

As connecting members useful for the dendrimers which are the subject of the invention, there may be mentioned groups of the type including alkyl, aryl, alkoxyalkyl, alkoxyaryl, alkylhydrazinoyl, arylhydrazinoyl, carboxyalkyl-hydrazido and in particular carboxymethyl-hydrazido, cyanoalkyl, allyl, propargyl, halocycloalkyl, haloalkoxyalkyl, alkylthioalkyl, haloalkylthioalkyl, aminoalkyl, N-alkylaminoalkyl, N,N-dialkylaminoalkyl, acylaminoalkyl, arylalkyl, phenyliminoalkyl, iminoaryl, imidoalkyl, amidoaryl, phosphoalkyl, phosphoryl, thiophosphoryl, phosphoraminoalkyl, phosphoraminoaryl, phosphoriminoalkyl, phosphoriminoaryl, phosphorimidoalkyl, phosphorimidoaryl, hydrazinoalkyl, hydrazinoaryl, allylidenealkylhydrazynoyl, allylidenearylhydrazinoyl, epoxybenzylidene, dialkylphosporimidoyl, diarylphosphorimidoyl, thioimidophosphoryl, thio-N-alkylazophosphoryl, thio-N-arylazophosphoryl optionally substituted with one or more groups chosen from the groups of the type including hydroxyl, mercapto, nitro, thiocyanate, azido, cyano, pentafluorosulfonyl, alkyl, aryl, haloalkyl, alkoxy, haloalkoxy, alkylthio, haloalkylthio, alkoxyalkyl, haloalkoxyalkyl, alkylthioalkyl, haloalkylthioalkyl, cyanoalkyl, cyanoalkoxy, cyanoalkylthio, alkylsulfinyl, haloalkylsulfinyl, alkylsulfonyl, haloalkylsulfonyl and alkoxysulfonyl, cycloalkyl, alkenyl, alkynyl, alkenyloxy, alkynyloxy, alkenylthio, alkynylthio, amino, N-alkylamino, N,N-dialkylamino, acylamino, hydroxy, alkoxy, carboxy, carbamoyl, N-alkylcarbamoyl, N,N-dialkylcarbamoyl, alkoxycarbonyl, acyl.

In addition to the core, the dendrons and the terminal functional groups, the dendrimers which are the subject of the invention comprise inner cavities inherently resulting from the existence of branches characteristic of the spatial structure of said dendrimers.

Said inner cavities allow in particular the inclusion of a variety of substances in the arborescent structure of said dendrimers which are the subject of the invention. However, the size and the accessibility of these inner cavities limits the inclusion of said substances to only the molecules whose size and properties are compatible therewith.

Said inner cavities of the dendrimers which are the subject of the invention have sizes which are generally between 0.001 and 30 nm$^3$, preferably between 0.01 and 10 nm$^3$.

The dendrimers which are the subject of the invention may be neutral dendrimers or dendrimers of the ionic type, either of the anionic or cationic type.

As dendrimers which are the subject of the invention which are neutral, there may be mentioned those whose terminal functional groups mainly consist of groups of the carboxylic acid type and/or of the phosphonic type and/or of the sulfonic, sulfonate or sulfate type and/or of the amine type.

As dendrimers which are the subject of the invention and which are of the ionic type, there may be advantageously mentioned the dendrimers whose terminal functional groups essentially comprise groups chosen from carboxylate and/or sulfonium and/or phosphonium and/or amidinium and/or guanidinium and/or ammonium groups, for example groups of the secondary, tertiary for quaternary ammonium type, most particularly groups of the pyridinium type.

As dendrimers which are the subject of the invention which are most particularly advantageous, there may be mentioned said dendrimers whose terminal functional groups essentially comprise groups of the N-hydrazinoylcarbonylmethyl-N,N,N-trialkylammonium halide type, among which groups there may be mentioned, by way of example, N-hydrazinoylcarbonylmethyl-N,N,N-tri-(n-propyl)ammonium chloride called Girard PR reagent or N-hydrazinoylcarbonylmethyl-N,N,N-trimethylammonium chloride represented by FIG. (V) below and which will be called Girard T reagent for the remainder of the present text; likewise there may be mentioned N-hydrazinoylcarbonylmethyl-N,N,N-pyridinium chloride called Girard P reagent.

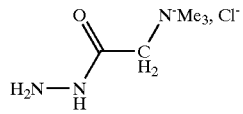

(V)

Preferably, the dendrimers which are the subject of the invention carry bonds between atoms from group V A of the periodic table of chemical elements, said group V A being as defined above in the present disclosure. More preferably, said dendrimers carry bonds between phosphorus atoms and nitrogen atoms.

These bonds between atoms from group V A of the periodic table of chemical elements may be present in the dendrimers which are the subject of the invention in quantities ranging from a few units to several thousands, or even several tens of thousands because of the large size which said dendrimers may have, for example the number of said bonds may be between 2 and 80,000, preferably between 20 and 20,000.

By way of purely illustrative example, FIG. (VIII) below gives a representation of such a dendrimer.

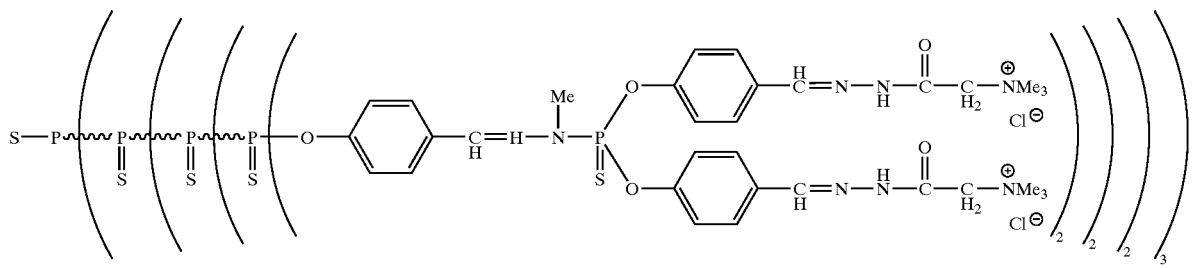

(VIII)

In addition to having as an essential characteristic the capacity to form gels, the dendrimers which are the subject of the invention most often allow the formation of gels which have the characteristic feature of being capable of comprising in their structure two types of volumes of insertion:
- the inner cavities characteristic of the branched structure of the dendrimers themselves;
- the so-called interstitial spaces derived from the three-dimensional structure of said gels which said dendrimers can form.

In other words, the inner cavities are within the actual dendrimers which are the subject of the invention while the interstitial spaces are outside the arborescent structure of said dendrimers.

Said inner cavities of the dendrimers according to the invention generally have sizes of between 0.001 and 30 nm$^3$, preferably between 0.01 and 10 nm$^3$.

The so-called interstitial spaces of the gels which the dendrimers which are the subject of the invention can form have sizes generally between 0.0005 and 50 $\mu$m$^3$, preferably between 0.001 and 20 $\mu$m$^3$.

Thus, by virtue of the numerous properties which characterize them and the main one of which is that they are capable of forming gels, the dendrimers which are the subject of the present invention may be used not only in compositions useful in the fields of agriculture and/or public health or domestic hygiene, as previously described, but also in a number of other fields advantageously using products, compositions or formulations having a gelled form. Thus, as products, compounds or other active substances which may be advantageously combined with the dendrimers which are the subject of the invention, there may be mentioned said products, compounds or other active substances useful in the fields of cosmetic, building or public works, in particular in association with coatings, paints or adhesives, in the textile sector, for example in association with dyes, or associated with inks for printing, but also in the agro-foodstuffs or pharmaceutical sectors or in the sectors for trapping various substances or compounds, in particular pollutants or catalytic compounds, or in the field of detergents, in particular laundry soaps, and in general in any field using compounds allowing encapsulation.

According to another particularly advantageous embodiment of the invention, the dendrimers according to the invention may be used to encapsulate active substances, preferably for encapsulating non-water-soluble or sparingly water-soluble active substances.

The expression sparingly or non-water-soluble describes substances whose solubility in water or in a substantially aqueous solvent make these substances particularly difficult to use or substances whose useful active properties are substantially reduced because of this difficulty or this impossibility of solubilizing them effectively.

Preparation of Novel Dendrimers

An additional aspect of the present invention consists in the methods for preparing the dendrimers which are the subject of the invention.

For the preparation of said dendrimers and as has been already mentioned in the present text, two types of methods may be mainly mentioned, divergent syntheses and convergent syntheses:

- in the divergent methods, the synthesis is carried out from the core toward the periphery by grafting an increasingly large number of small molecules onto the surface of the dendrimer possessing multiple chemical functional groups, a representation of such a route of synthesis is given by scheme (III):
- in the convergent methods, the synthesis is carried out from the periphery toward the core by combining with each other increasingly larger molecules constantly having an available chemical functional group at the level of the core, a representation of such a route of synthesis is given by scheme (IV).

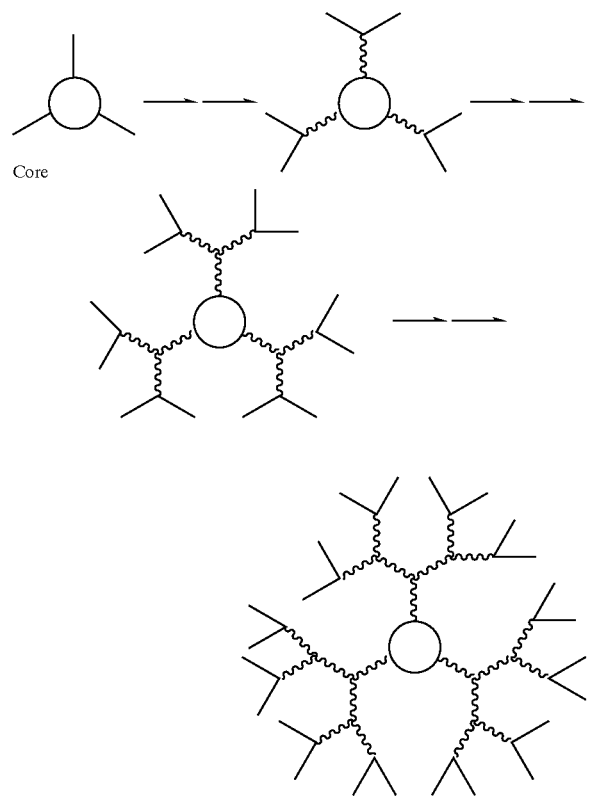

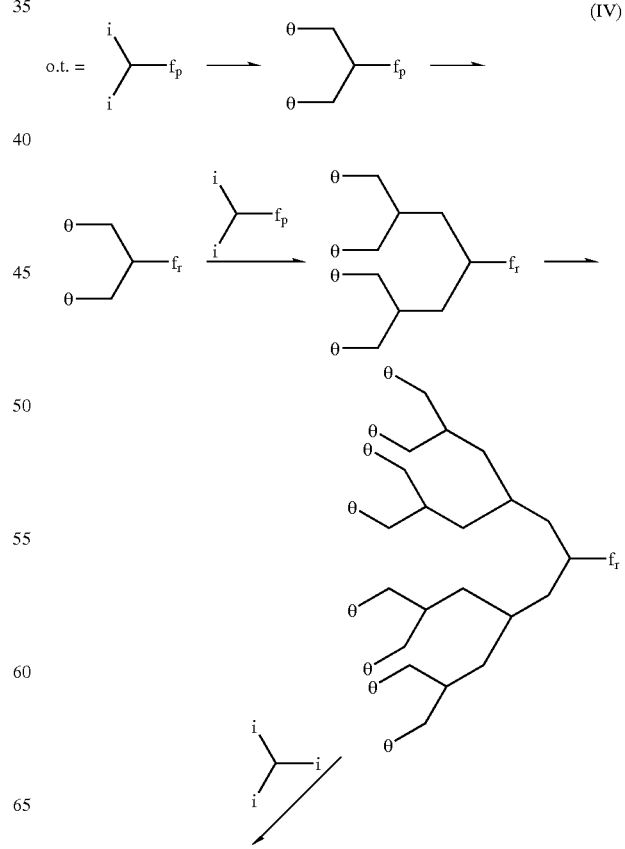

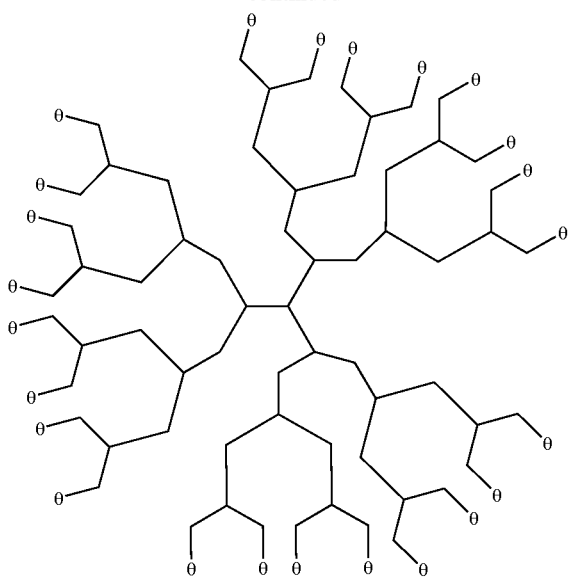

$f_r$ = reactive functional group
$f_p$ = protected functional group
$\theta$ = surface
i = inside Preferably, the preparation of the dendrimers which are the subject of the invention uses the so-called divergent routes of synthesis, that is to say the routes of synthesis for which the growth of said dendrimers occurs from the core toward the periphery of said dendrimers, most often by cascade reactions.

More preferably, the preparation of the dendrimers which are the subject of the invention is characterized by reacting a dendrimer whose terminal functional groups essentially consist of an aldehyde type functional group with a so-called Girard reagent as previously described, preferably a Girard T reagent carrying a trimethylammonium group or a Girard PR reagent carrying a tri-(n-propyl)ammonium group or a so-called Girard P reagent carrying a pyrridinium group.

By way of example, a method for preparing the dendrimer represented by FIG. (X) below is given in greater detail in the present text.

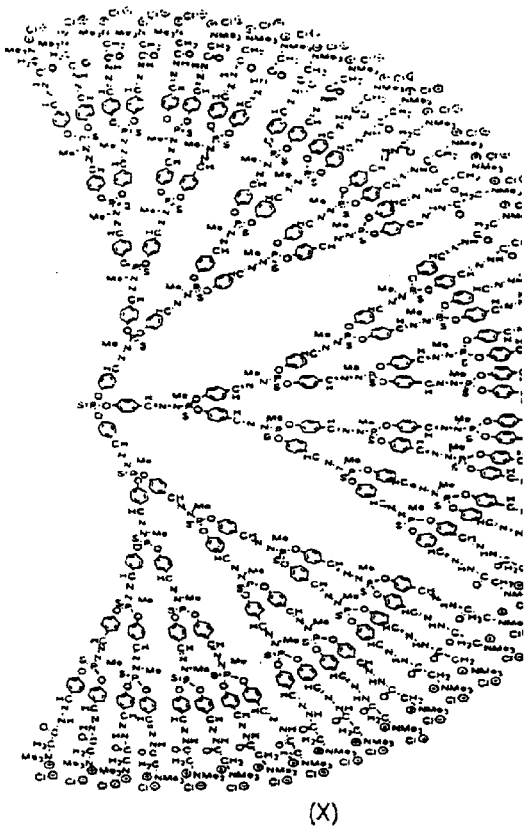
(X)

To facilitate understanding of the remainder of the present disclosure, the dendrimer represented by FIG. (X) and whose terminal functional groups comprise chemical radicals derived from Girard T reagents is called dendrimer G'4-T.

For the preparation of said dendrimer G'4-T, a dendrimer termed G'4-CHO is normally used whose terminal functional groups essentially comprise aldehyde type groups at the periphery, preferably all said terminal functional groups consist of aldehyde-type groups at the periphery; said dendrimer G'4-CHO may be prepared with reference to the information given in the manual Les dendrimères previously cited in the present disclosure. For the preparation of said dendrimer G'4-CHO, the reaction scheme represented by FIG. (XI) below may be followed for example.

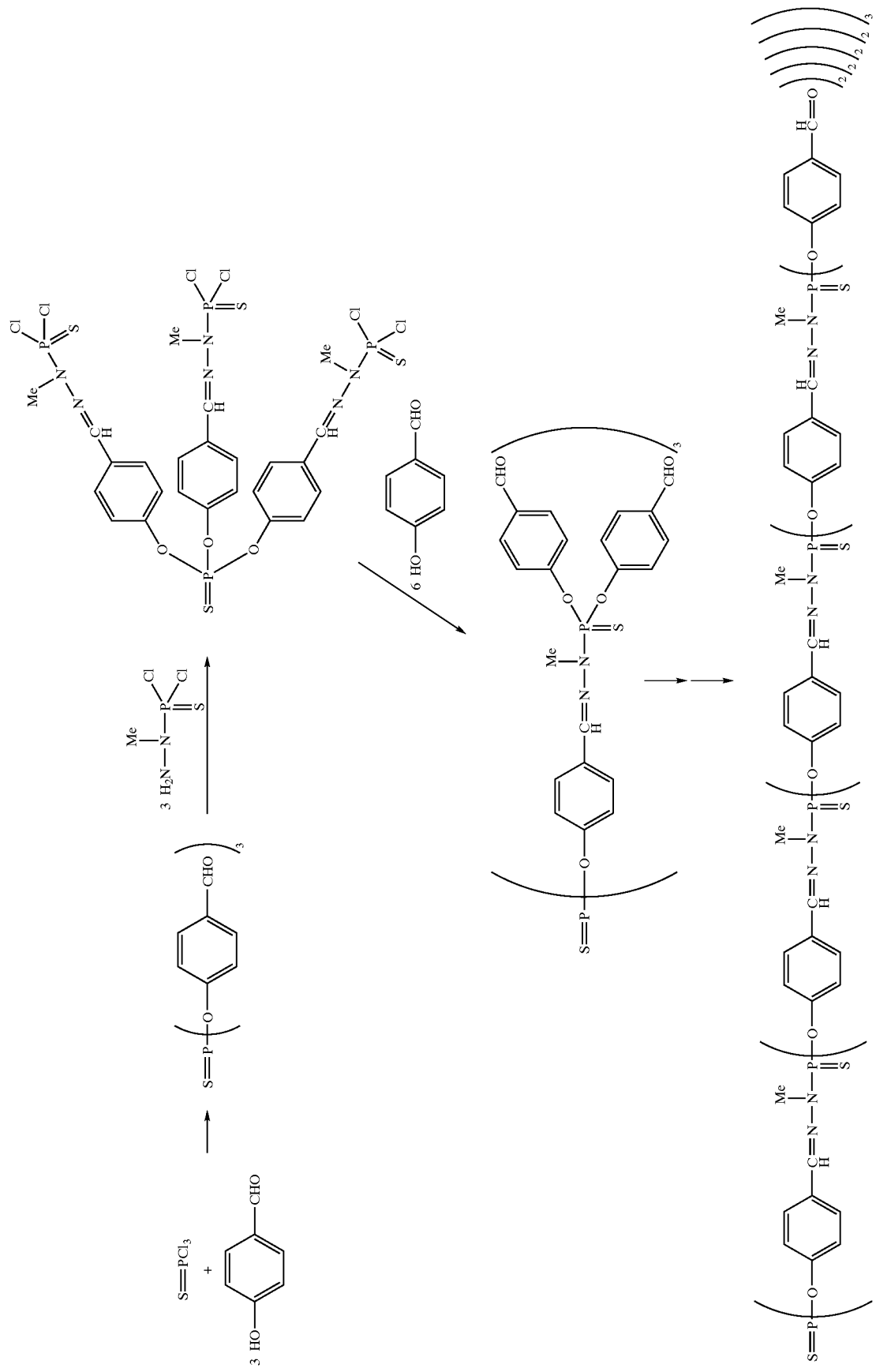

It is then possible to react said dendrimer G'4-CHO in the presence of the so-called Girard T reagent as described above in the present text and a representation of which is given below by FIG. (V), and thus to obtain the dendrimer termed G'4-T.

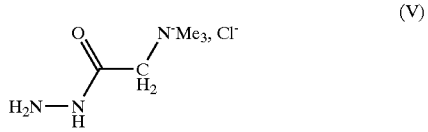

Using a method of preparation similar to that described above for the preparation of dendrimer G'4-T, it is possible to prepare a dendrimer termed G'4-P whose terminal functional groups comprise chemical radicals derived from Girard P reagents.

The methods of treatment and/or protection using the compositions according to the invention which are described in the present disclosure also form part of said invention. Among said methods of treatment, those which are preferred are those for treatment or protection which are useful in the fields of agriculture and/or public health or domestic hygiene.

Methods of Treatment and/or Protection Useful in the Field of Agriculture, in Particular for the Treatment of Crops The methods for the treatment or protection of crops according to the invention have the essential characteristic of comprising the step of using an effective and non-phytotoxic quantity of one or more compositions according to the invention.

The expression effective and non-phytotoxic quantity is understood to mean, within the meaning of the present disclosure, a quantity of composition according to the invention sufficient to allow the control and/or destruction and/or eradication in particular of diseases and/or fungi and/or weed plants and/or insect or animal pests present or capable of appearing on crops, and to allow satisfactory control of the growth of said crops, and causing no phytoxicity symptom for said crop.

Such a quantity is capable of varying within fairly wide limits, in particular according to the crops treated, the needs, the nature of the diseases to be treated, of the insects and/or animal pests, the weed plants, to be controlled, destroyed or eradicated, the degree of infestation of these pests, the climatic and/or edaphic conditions, and the active substance (s) contained in the compositions according to the invention which are used.

The compositions according to the invention are most often used in quantities of between 1 g/ha and 5 kg/ha.

The methods for the treatment and/or protection of crops according to the invention may in particular use the compositions according to the invention previously diluted or dispersed in an appropriate quantity of water.

METHODS of Treatment Useful in the Field of Public Health or Domestic Hygiene

As regards the methods of treatment or protection according to the invention which are useful in public health or domestic hygiene, they are mainly characterized by the use of one or more compositions according to the invention which are described above, particularly one or more of said compositions in gelled form.

Said methods of treatment which are useful in public health or domestic hygiene use effective quantities of said compositions which make it possible to control, destroy or eradicate the insects and/or animal pests present or capable of appearing, but also effective quantities of compositions according to the invention containing one or more active substances regulating the growth of said insect and/or animal pests.

Said quantities may vary, in particular according to the degree of infestation of these insect and/or animal pests to be controlled, destroyed or eradicated or according to the climatic conditions or according to the pesticide and/or growth regulating active substance used. Quantities of composition according to the invention, in particular in bait form, of the order of 0.1 to 200 $g/m^2$ are generally quite suitable.

Advantageously, the various methods of treatment and/or protection according to the invention which have been described, both those which use a gelled composition according to the invention and those using a pulverulent composition according to the invention, may use said compositions in numerous forms and in particular in ground, minced, chopped, truncated, crushed, flattened, compressed, pressed, pounded, laminated, pulverized, milled, comminuted, disintegrated, fragmented, dispersed, cut, divided, sectioned, sliced or fractionated form.

Although it has been possible for some of the various aspects of the present invention to be described by particular characteristics or according to advantageous or preferred forms, it should be noted that the disclosure of said aspects by said particular characteristics or in advantageous or preferred forms is only given by way of example and that numerous variations of the details of said aspects of the invention, in particular of preparation, use or combination, may be envisaged without departing from the spirit or the scope of the present invention.

Likewise, it should be noted that the sole objective of the use of subheadings in the disclosure of the various aspects of the present invention is to provide greater clarity to the present disclosure and this use cannot at all be considered as limiting the scope of said invention.

Examples are given below to allow better illustration of the various aspects of the present invention, they do not therefore in any way limit the scope thereof.

Examples 1 and 2 give an illustration of methods for the preparation of compositions according to the invention, while Example 3 makes it possible to illustrate the aspect of the present invention relating to the preparation of the dendrimers which are the subject of said invention.

EXAMPLE 1

For the preparation of a composition according to the invention, the procedure is carried out as follows: 35 g of dendrimer of formula (X) called G'4-T, 50 g of propylene glycol as antigel, 5 g of a wetting agent of the ethoxylated polyalcohol type and 6 g of an antifoaming agent of the silicone oil type are added to 724 g of water. 200 g of Fenamidone, a fungicide active substance whose chemical name is (4-S)-4-methyl-2-methylthio-4-phenyl-1-phenylamino-2-imidazolin-5-one are dispersed in the solution obtained. 25 g of a thickening agent of the silicoaluminate type are then added. After storing the above-prepared mixture for 14 days at 54° C., a composition according to the invention is obtained.

EXAMPLE 2

The method of preparation of Example 1 is repeated by replacing the 200 g of fungicide active substance with 200 g of an insecticide active substance, Fipronil having the chemical name 5-amino-3-cyano-1-(2,6-dichloro-4-trifluoromethyl)phenyl-4-trifluoromethylsulfinylpyrazole, and the 35 g of dendrimer G'4-T by 35 g of dendrimer G'4-P as previously described and whose terminal functional groups essentially comprise the radicals derived from the so-called Girard P reagents carrying pyridinium groups. A composition is obtained in gelled form according to the invention which, when applied in an amount of about 0.1 g of active substance per 100 m$^2$ of surface to be protected constitutes an effective bait against cockroaches, in particular of the *Germanica blatella* type.

EXAMPLE 3

This example proposes to give a particular illustration of the aspect of the present invention relating to the preparation of a composition according to the invention.

1.8% by mass of dendrimer G4-P is added, at a temperature of about 45° C., to a known formulation (200 g/l of Fipronil as insecticide active substance, 400 g/l of refined corn oil, 50 g/l of propylene glycol as antigelling agent, 13 g/l of an emulsifying agent, 25 g/l of a dispersing agent, 5 g/l of a wetting agent, 8 µl of another wetting agent, 5 µl of an antifoaming agent, 344 g/l of water as liquid carrier) of the flowable concentrate type comprising 200 g/l of Fipronil as active substance.

The mixture obtained is then placed in an oven at a temperature of about 60–65° C.

After two days, a composition according to the invention is obtained which is in the form of a cuttable gel.

EXAMPLE 4

For the preparation of the dendrimer G'4-T represented by FIG. (X), the procedure may be carried out in the following manner: 100 ml of an aqueous solution containing 5.23 g of so-called Girard T reagent are added to 10 g of dendrimer G'4-CHO dissolved in 190 ml of tetrahydrofuran. The reaction medium thus obtained is kept stirring at room temperature for about 15 hours. After that, said reaction medium is heated at 35° C. for about 4 days. The solvents are then removed from said reaction medium and the solid thus obtained is then washed with 300 ml of tetrahydrofuran, with stirring. The dendrimer G'4-T is thus obtained in the form of a powder with a white appearance which is then dried. The overall yield of the present method of preparation is quantitative.

What is claimed is:

1. A gelled composition for use in agriculture, public health or domestic hygiene, characterized in that it comprises at least one active substance and at least one gellable dendrimer; wherein said dendrimer comprises a core, a plurality of branches linked to the core and terminal groups linked directly or indirectly through a connector to branches and has between 2 and 20,000 phosphorus to nitrogen bonds; wherein said gelled composition is in the form of a gel and contains a liquid carrier.

2. The composition as claimed in claim 1, characterized in that the amount of active substance(s) present is between 0.5 and 99.99% and the amount of dendrimer of between 0.028 and 99.5% by weight.

3. The composition as claimed in claim 1, characterized in that the gellable dendrimer is such that when mixed with or solubilized in water in respective proportions by weight of 28.5/98.5, at a temperature of about 65° C., forms after 48 hours, a gelled product which does not flow when it is placed in the form of a cubic mass on a flat surface.

4. The composition as claimed in claim 1, characterized in that the active substance(s) is (are) present in a quantity of between 5 and 70% by weight, and the dendrimer is such that when mixed with or solubilized in water in respective proportions by weight of 28/28 at room temperature forms, after two weeks, a gelled product which does not flow when it is placed in the form of a cubic mass on a flat surface.

5. The composition as claimed in claim 1, characterized in that the dendrimer is such that after mixing with or solubilizing in water in respective proportions by weight of 28.8/98.2 at a temperature between 40 and 65° C. and is then heated for 4 weeks at a temperature of about 60–65° C., forms a gelled product which does not flow when it is placed in the form of a cubic mass on a flat surface.

6. The composition as claimed in claim 1, characterized in that the dendrimer is a neutral dendrimer having terminal groups selected from the group consisting of carboxylic acid, phosphonic acid, sulfonic acid, sulfonate, sulfate and amine groups, or is an ionic dendrimer having terminal groups selected from the group consisting of carboxylate, sulfonium, phosphonium, amidinium, guanidinium and ammonium groups.

7. The composition as claimed in claim 1, characterized in that the dendrimer connector comprises a 2 to 50 atom hydrocarbon moiety, optionally substituted, optionally heteroatom-containing, hydrocarbon radical.

8. The composition as claimed in claim 1, characterized in that the dendrimer core comprises a 1 to 30 atom hydrocarbon moiety which optionally contains at least one heteroatom selected from the group consisting of oxygen, sulfur, nitrogen, phosphorus and halogen, a hexachlorocyclotriphosphazene moiety or a trichlorothiophosphane moiety.

9. The composition as claimed in claim 1, characterized in that the dendrimer branches comprise hydrocarbon radicals which optionally contain at least one heteroatom selected from the group consisting of oxygen, sulfur, nitrogen, phosphorus and halogen.

10. The composition as claimed in claim 1, characterized in that at least 10% of the dendrimer branches have the same chemical motif in that they are composed of the same elements and have the same unsaturation or lack thereof.

11. The composition as claimed in claim 1, characterized in that the liquid carrier comprises water or at least one organic solvent and the quantity of carrier is present up to 99% by weight.

12. The composition as claimed in claim 1, characterized in that at least 50% of the active substance is releasable from the composition.

13. The composition as claimed in claim 12, characterized in that at least 80% of the active substance is releasable from the composition.

14. A method for the preparation of a pulverulent material, characterized in that it comprises providing a composition as claimed in claim 1, and at least partially removing the carrier from the composition.

15. A method for the preparation of a pulverulent material according to claim 14, characterized in that the composition from which at least part of the carrier has been removed is ground.

16. A method for treatment or protection of crops by applying to said crops the composition of claim 1.

17. A gelled composition for use in agriculture, public health or domestic hygiene, characterized in that it comprises at least one active substance selected from the group consisting of herbicides, fungicides, insecticides, acaricides, rodenticides, nematocides, repellents and plant growth regulators and at least one gellable dendrimer; wherein said dendrimer comprises a core, a plurality of branches has between 20 and 20,000 phosphorus to nitrogen bonds linked to the core and terminal groups linked directly or indirectly through a connector to branches, wherein said gelled composition is in the form of a pulverulent composition; and wherein at least 50% of the active substance is releasable from said pulverulent composition.

18. The composition as claimed in claim 17, characterized in that it contains a quantity of liquid carrier which is insufficient to convert said pulverulent composition into a gel.

19. The pulverulent composition as claimed in claim 17, characterized in that the quantity of active substance(s) is between 2 and 99.99% and the quantity of dendrimer of between 0.01 and 99.5% by weight.

20. The pulverulent composition as claimed in claim 19, characterized in that the quantity of active substance(s) is between 5 and 95% by weight and the quantity of dendrimer of between between 0.5 and 50% by weight.

21. A method for treatment or protection of crops by applying to said crops the composition of claim 17.

22. A gelled composition for use in agriculture, public health or domestic hygiene, characterized in that it comprises at least one active substance and at least one gellable dendrimer; wherein said dendrimer comprises a core, a plurality of branches linked to the and terminal groups linked directly or indirectly through a connector to branches has between 20 and 20,000 phosphorus to nitrogen bonds, is ionic, and has terminal groups selected from the group consisting of secondary, tertiary, or quaternary ammonium or pyridinium groups; and wherein said gelled composition contains a liquid carrier and is in the form of a gel.

23. A gelled composition for use in agriculture, public health or domestic hygiene, characterized in that it comprises at least one active substance and at least one gellable dendrimer; wherein said dendrimer comprises a core, a plurality of branches linked to the core and terminal groups linked directly or indirectly through a connector to branches, and has between 20 and 20,000 phosphorus to nitrogen bonds; and wherein said gelled composition contains a liquid carrier and is in the form of a gel.

24. A gelled composition for use in agriculture, public health or domestic hygiene, characterized in that it comprises at least one active substance and at least one gellable dendrimer; wherein said dendrimer comprises a core, a plurality of branches linked to the core and terminal groups linked directly or indirectly through a connector to branches has between 20 and 20,000 phosphorus to nitrogen bonds, and has at least one insertion volume selected from the group consisting of an inner cavity defined by the dendrimer branches having a size between 0.001 and 30 mm$^3$; and an interstitial space of the three-dimensional structure of the gel having a size between 0.0005 and 50 $\mu$m$^3$;

and wherein said gelled composition contains a liquid carrier and is in the form of a gel.

25. The composition as claimed in claim 24, characterized in that it comprises between 0.1 and 60% by weight of gellable dendrimer having at least one insertion volume selected from the group consisting of an inner cavity having a size between 0.01 and 10 nm$^3$; and an interstitial space of the three-dimensional structure of the gel having a size between 0.001 and 20 $\mu$m$^3$.

26. The composition as claimed in claim 24, characterized in that at least half of the active substance(s) is(are) contained in the interstitial spaces of the three-dimensional structure of the gel.

27. A method for preparing a composition for use in agriculture, public health or domestic hygiene, wherein said composition comprises at least one active substance and at least one gellable dendrimer; wherein said dendrimer comprises a core, a plurality of branches linked to the core and terminal groups linked directly or indirectly through a connector to branches and has between 20 and 20,000 phosphorus to nitrogen bonds; and wherein said gelled composition contains a liquid carrier and is in the form of a gel, characterized in that said method comprises:

a) solubilizing a mixture comprising said at least one active substance, at least one gellable dendrimer and liquid carrier; and b) heating said mixture for 0.25 to 45 days at a temperature of about 60–65° C.

28. A pulverulent material obtained by a process comprising providing a composition comprising at least one active substance and at least one gellable dendrimer, wherein said dendrimer comprises a core, a plurality of branches linked to the core and terminal groups linked directly or indirectly through a connector to branches and has between 2 and 20,000 phosphorus to nitrogen bonds; and wherein said composition contains a liquid carrier and is in the form of a gel, and at least partially removing the carrier therefrom.

29. A method of treatment or protection of a surface by applying a gelled composition to said surface in an amount between 0.1 and 200 g/m$^2$ of surface; wherein said gelled composition comprises at least one active substance and at least one gellable dendrimer; wherein said dendrimer comprises a core, a plurality of branches linked to the core and terminal groups linked directly or indirectly through a connector to branches and has between 20 and 20,000 phosphorus to nitrogen bonds; and wherein said gelled composition is in the form of a pulverulent composition or a gel.

* * * * *

UNITED STATES PATENT AND TRADEMARK OFFICE
CERTIFICATE OF CORRECTION

PATENT NO. : 6,939,831 B1  Page 1 of 1
DATED : September 6, 2005
INVENTOR(S) : Caminade et al.

It is certified that error appears in the above-identified patent and that said Letters Patent is hereby corrected as shown below:

<u>Title page,</u>
Item [54], Title, should read -- PESTICIDE AND/OR PLANT GROWTH REGULATING COMPOSITIONS --.

Signed and Sealed this

Thirtieth Day of May, 2006

JON W. DUDAS
*Director of the United States Patent and Trademark Office*